(12) United States Patent
Krismer et al.

(10) Patent No.: US 10,774,113 B2
(45) Date of Patent: Sep. 15, 2020

(54) ANTI-INFECTIVE COMPOUND

(71) Applicant: Eberhard Karls Universitaet Tuebingen, Tuebingen (DE)

(72) Inventors: Bernhard Krismer, Kirchentellinsfurt (DE); Andreas Peschel, Leinfelden-Echterdingen (DE); Stephanie Grond, Tuebingen-Hirschau (DE); Alexander Zipperer, Tuebingen (DE); Martin Christoph Konnerth, Tuebingen (DE); Daniela Janek, Tuebingen (DE); Hubert Kalbacher, Tuebingen (DE); Nadine Anna Schilling, Tuebingen (DE)

(73) Assignee: Eberhard Karls Universitaet Tuebingen, Tuebingen (DE)

( * ) Notice: Subject to any disclaimer, the term of this patent is extended or adjusted under 35 U.S.C. 154(b) by 0 days.

(21) Appl. No.: 15/713,103

(22) Filed: Sep. 22, 2017

(65) Prior Publication Data
US 2018/0155397 A1 Jun. 7, 2018

Related U.S. Application Data

(63) Continuation-in-part of application No. PCT/EP2016/056358, filed on Mar. 23, 2016.

(30) Foreign Application Priority Data

Mar. 23, 2015 (EP) .................................... 15160285

(51) Int. Cl.
*A61K 38/12* (2006.01)
*C07K 7/56* (2006.01)
(Continued)

(52) U.S. Cl.
CPC .............. *C07K 7/56* (2013.01); *A61K 35/741* (2013.01); *A61K 38/12* (2013.01); *A61K 38/15* (2013.01);
(Continued)

(58) Field of Classification Search
CPC .......... A61K 38/12; A61K 38/15; C07K 7/56; C07K 11/02
See application file for complete search history.

(56) References Cited

U.S. PATENT DOCUMENTS 8,809,494 B2 * 8/2014 Bergman ............. C07K 14/445
530/300
9,458,200 B2 10/2016 Kalesse et al.
(Continued)

FOREIGN PATENT DOCUMENTS

CN 101845081 A 9/2010
DE 102005055944 A1 7/2007
(Continued)

OTHER PUBLICATIONS

Krismer et al. Nutrient Limitation Governs *Staphylococcus aureus* Metabolism and Niche Adaptation in the Human Nose. PLOS Pathogen. Jan. 16, 2014, vol. 10, Issue 1, e1003862. (Year: 2014).*
(Continued)

*Primary Examiner* — Jeffrey E. Russel
(74) *Attorney, Agent, or Firm* — Marshall, Gerstein & Borun LLP

(57) ABSTRACT

The invention relates to novel infective agents, the use thereof for the production of a pharmaceutical composition for the treatment and prophylaxes of a disease, preferably an infectious disease, a pharmaceutical composition comprising said compound, and to methods of producing said compounds. The invention further relates to a new probiotic configured for preventing or reducing the colonization by a pathogenic microorganism of an organ of a living being.

31 Claims, 11 Drawing Sheets
Specification includes a Sequence Listing.

(51) Int. Cl.

| | | |
|---|---|---|
| *A61K 38/15* | (2006.01) | |
| *C07K 11/02* | (2006.01) | |
| *A61P 31/04* | (2006.01) | |
| *A61K 35/741* | (2015.01) | |
| *C12P 21/02* | (2006.01) | |
| *A61K 38/00* | (2006.01) | |

(52) U.S. Cl.
CPC .............. *A61P 31/04* (2018.01); *C07K 11/02* (2013.01); *C12P 21/02* (2013.01); *A61K 38/00* (2013.01)

(56) References Cited

U.S. PATENT DOCUMENTS

2005/0244914 A1* 11/2005 Liu ...................... A61K 31/519
 435/21
2009/0239216 A1 9/2009 Sasatsu et al.
2014/0357563 A1* 12/2014 Poncz ................ A61K 38/1709
 514/13.8

FOREIGN PATENT DOCUMENTS

| EP | 0932613 A1 | 8/1999 |
|---|---|---|
| JP | 2011-525512 A | 9/2011 |
| WO | WO-2006/073133 A1 | 7/2006 |

OTHER PUBLICATIONS

Zipperer et al. Human commensals producing a novel antibiotic impair pathogen colonization. Nature. Jul. 28, 2016, vol. 535, pp. 511-516. (Year: 2016).*

Carnio et al., Pyridinyl polythiazole class peptide antibiotic micrococcin P1, secreted by foodborne *Staphylococcus equorum* WS2733, is biosynthesized nonribosomally, Eur. J. Biochem., 268(24):6390-401 (2001).

Heilbronner et al., Genome sequence of *Staphylococcus lugdunensis* N920143 allows identification of putative colonization and virulence factors, FEMS Microbiol. Lett., 322(1):60-7 (2011).

Krismer et al., Nutrient limitation governs *Staphylococcus aureus* metabolism and niche adaptation in the human nose, PLoS Pathog., 10(1):e1003862 (2014).

Martin et al., Kocurin, the true structure of PM181104, an antimethicillin-resistant *Staphylococcus aureus* (MRSA) thiazolyl peptide from the marine-derived bacterium Kocuria palustris, Mar. Drugs, 11(2):987-98 (2013).

Tabata et al., Zelkovamycin, a new cyclic peptide antibiotic from *Streptomyces* sp. K96-0670. II. Structure elucidation, J. Antibiot., 52(1):34-9 (1999).

Wanke et al., *Staphylococcus aureus* skin colonization is promoted by barrier disruption and leads to local inflammation, Exp. Dermatol., 22(2):153-5 (2013).

Wyatt et al., *Staphylococcus aureus* nonribosomal peptide secondary metabolites regulate virulence, Science, 329(5989):294-6 (2010).

Donia et al., Mollamides B and C, Cyclic hexapeptides from the Indonesian tunicate Didemnum molle, J. Nat. Prod., 71(6):941-5 (2008).

Ferrari et al., Antibiotics A21459 A and B, new inhibitors of bacterial protein synthesis. II. Structure elucidation, J. Antibiot. (Tokyo), 49(2):150-4 (1996).

Igarashi et al., Pargamicin A, a novel cyclic peptide antibiotic from *Amycolatopsis* sp, J. Antibiot. (Tokyo), 61(6):387-93 (2008).

International Search Report and Written Opinion, International Application No. PCT/EP2016/056358, dated Jun. 8, 2016.

Jones, Amino Acids and Peptides, Royal Society of Chemistry, vol. 23, pp. 166-170 (Jan. 1, 1992).

* cited by examiner

☒ S.aureus  ☐ S.lugdunensis WT

☒ S.aureus  ☐ S.lugdunensis Δnrps4

☒ S.aureus  ☐ S.lugdunensis Δnrps4

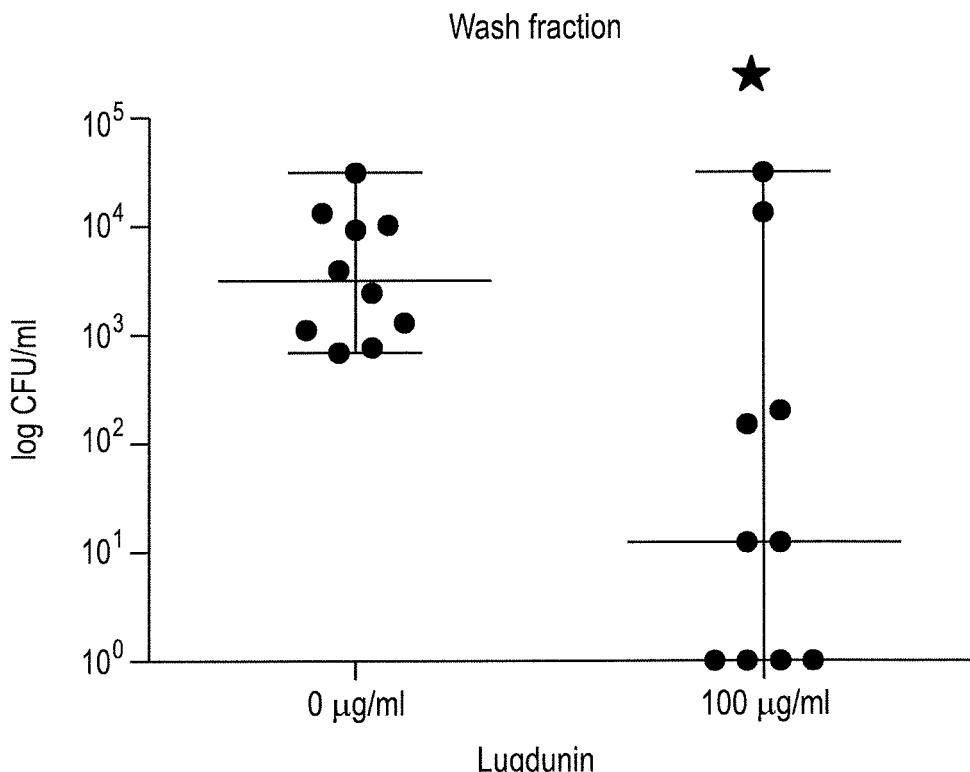
Fig. 8
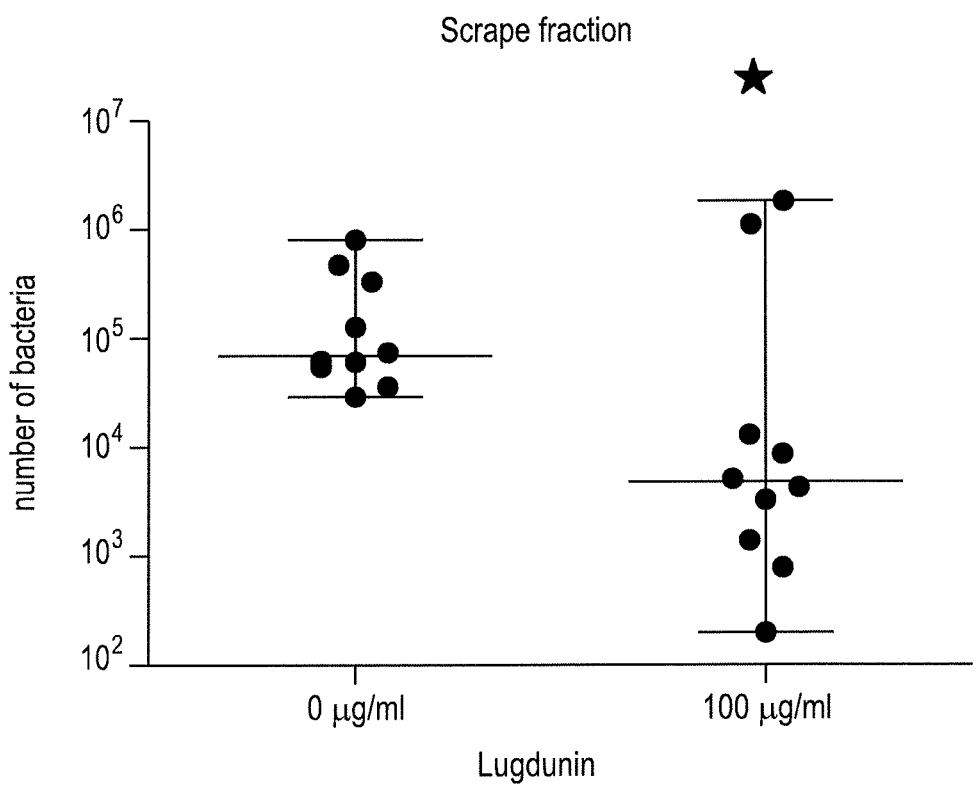

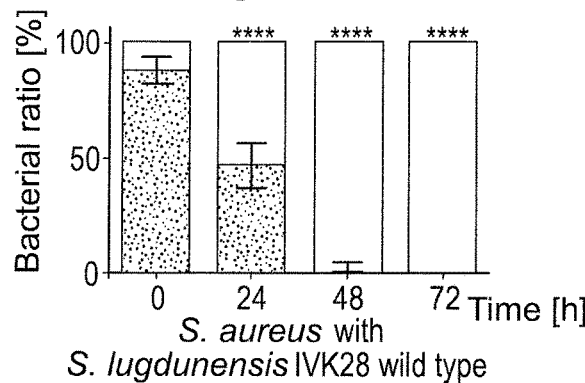
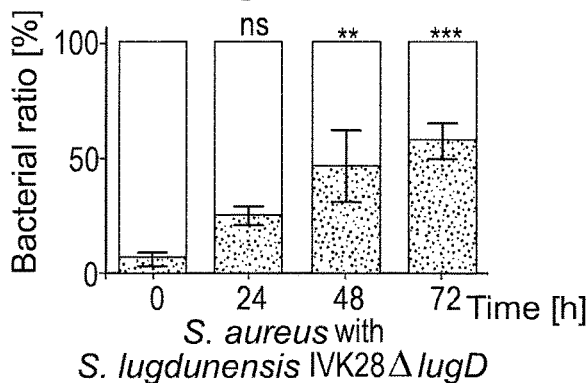
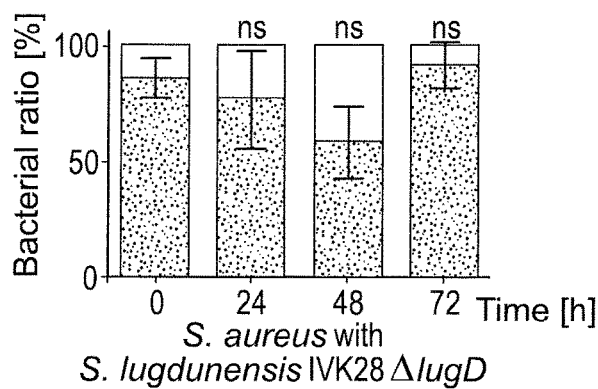
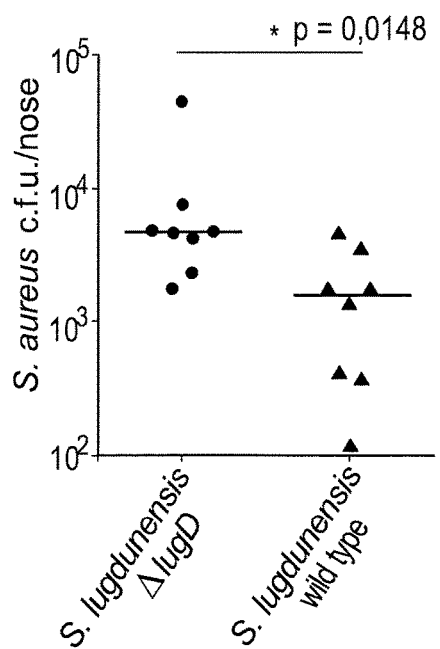
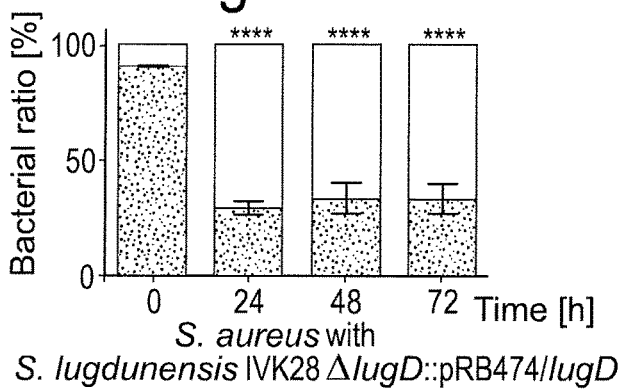

SEQUENCE LISTING

```
<160> NUMBER OF SEQ ID NOS: 1

<210> SEQ ID NO 1
<211> LENGTH: 29605
<212> TYPE: DNA
<213> ORGANISM: Staphylococcus lugdunensis
<220> FEATURE:
<221> NAME/KEY: source
<222> LOCATION: (1)..(29605)
<223> OTHER INFORMATION: /mol_type="DNA" /note="nrp-operon IVK28"
      /organism=Staphylococcus lugdunensis
<220> FEATURE:
<221> NAME/KEY: misc_feature
<222> LOCATION: (427)..(936)
<220> FEATURE:
<221> NAME/KEY: misc_feature
<222> LOCATION: (1027)..(1266)
<223> OTHER INFORMATION: /allele="put. negative regulator of sigY (in
      Bacillus)"
<220> FEATURE:
<221> NAME/KEY: misc_feature
<222> LOCATION: (1253)..(2143)
<223> OTHER INFORMATION: /allele="ABC transporter (GdmF type multidrug
      transport system)"
<220> FEATURE:
<221> NAME/KEY: misc_feature
<222> LOCATION: (2140)..(2904)
<223> OTHER INFORMATION: /allele="ABC-2 type transport system permease
      protein"
<220> FEATURE:
<221> NAME/KEY: misc_feature
```

```
<222> LOCATION: (2917)..(3630)
<223> OTHER INFORMATION: /allele="ABC transporter"
<220> FEATURE:
<221> NAME/KEY: misc_feature
<222> LOCATION: (3623)..(5164)
<223> OTHER INFORMATION: /allele="hyp. membrane protein"
<220> FEATURE:
<221> NAME/KEY: misc_feature
<222> LOCATION: (5409)..(5981)
<223> OTHER INFORMATION: /allele="TetR/AcrR family regulator"
<220> FEATURE:
<221> NAME/KEY: misc_feature
<222> LOCATION: (6007)..(13131)
<223> OTHER INFORMATION: /allele="lugA (corresponds to SLUG_08100 of
      Staphylococcus lugdunensis N920143"
<220> FEATURE:
<221> NAME/KEY: misc_feature
<222> LOCATION: (10338)..(10347)
<223> OTHER INFORMATION: /allele="Tn917 insertion site"
<220> FEATURE:
<221> NAME/KEY: misc_feature
<222> LOCATION: (13121)..(17341)
<223> OTHER INFORMATION: /allele="lugB corresponds to the fused sequence
      of SLUG_08110 and SLUG_08120 (by insertion of one additional
      nucleotide) of Staphylococcus lugdunensis N920143"
<220> FEATURE:
<221> NAME/KEY: misc_feature
<222> LOCATION: (17359)..(26172)
<223> OTHER INFORMATION: /allele="lugC corresponds to SLUG_08130 of
      Staphylococcus lugdunensis N920143"
<220> FEATURE:
<221> NAME/KEY: misc_feature
<222> LOCATION: (26169)..(26855)
<223> OTHER INFORMATION: /allele="thioesterase family protein"
<220> FEATURE:
<221> NAME/KEY: misc_feature
<222> LOCATION: (26893)..(28632)
<223> OTHER INFORMATION: /allele="lugD corresponds to SLUG_08150 of
      Staphylococcus lugdunensis N920143"
<220> FEATURE:
<221> NAME/KEY: misc_feature
<222> LOCATION: (28640)..(29293)
<223> OTHER INFORMATION: /allele="4'-phosphopantetheinyltransferase"

<400> SEQUENCE: 1
aggtcttaaa aaagcacgtc gttctccaca attctcaaaa cgttaattgt tggaagaaat      60
atacaaaaca cctcgatatt atgtcgaggt gttttttgtg gaaaaattca gtatattgtg     120
tcttgatatt taaccaatct ttctaggatt aacttgagag gtatatataa aacatattac     180
actatactat tacgaaaaag atttctggag gaactactgt ttgacgtttt aaaactccat     240
ctaacagtct tttaaagaga gatatatgat gtgttcgtat acctattaca aaagtaggaa     300
aatcaaatta tattattaca gtcaatgtgg ccgatgttga ttttggcaat atagtcataa     360
gaaataatca tatgaaccac agtattaata gttttaactt ttgctagtaa agtgaatcaa     420
aattggttat ggaataataa caagtgaaat ggttcgctct ttgttattcg tattttgttt     480
ttcattgtaa tatttattaa ttaaacagtt aagatcggac tggaaatttt caaattcact     540
gttttctaaa tttagttttg aaatagaaaa ggtagcttta tcatccttat taattgtttt     600
atgataattt tgataagatt gtaatacata cataaaataa taagtaacaa agtctatttt     660
tttactgtaa ttcgcttgag tccactctgt ttcatcaatt ttatagcctt tagagtttat     720
tgcataatag ttttcttcac tagaacgtaa tttttttggtc tttacaattt ttaataattg     780
ttcttcaaac atagcattta catgtctata cagtgttgct tgaggcacat cttctaataa     840
ttcattgagt tgcataatag aaagtccttc tggtttatcg attaatgtta atgcgatttt     900
aaaacgtgtt tgattttaa ataaactgaa ttccatacat aacacctcac tttatacata     960
ataattgatt tttaaataaa tgtacagtaa cattatcatt atcaataatg ataatggagg    1020
```

```
gtgaaaatga atactgatat taacgtctta aagaaatag actgggggac tattatgcca      1080
atattaatac caatattggt tttacatgta gtacttttaa taattgccct aatcgattta      1140
tatagacgaa gaaaattgt taattatcct attgcttggg caatcgcaat tttgttgttt      1200
aatactattg gacctattct ttatttgatt attggaagga ggctaataaa aattgatcga      1260
gattaagcat gtgaataaaa tgtttagagg aagaaaaata ctgaaaaata tttctttta      1320 tatttcagag ggagagtgta ttggattatt aggtcctaat ggtgctggga aaacaacatt      1380
gattaaatgt attactggaa ttattaatta tgaaaaggg gaaattaaat ttaatggaaa      1440
aaatattttg aatttaaaa atgatattgg ttatttatca cagcacacag attttaagca      1500
gtggatgact tgtgaagagt cgttaagatt ttttggtggt ttatcaggtt taaataaaac      1560
gtatattgct cagaatatta ataaaatact aaaagatgta ggtcttcaga ataaaaataa      1620
atataaggta gaagaattat caggagggat gaaacagaga ttaggcatag cacaggctat      1680
tttacatcgt ccaaagtttt tggtcttaga tgaaccagta tcagctcttg atccagttgg      1740
caggaatgaa atcaaaaacc taataaaaaa attgaaaaaa tacacaacag ttcttatatc      1800
cacacatatt cttgatgatg caagtgaatt ttgtgatcga tatattatta taaaagatgg      1860
agaaatcatc ggaaatataa ccaatgaaga tgagactgtg aattacaaaa gtatatattt      1920
aaaaatttct ttaaaagatt cttatgatcc ggatattcaa ttaaccgact tatatgattt      1980
acaaaaagta aaagcaggag aatatattgt aaccagtcga aagccaattg aaatatctga      2040
gttaattgaa gaactggaca aaattaatat taaagtgaat tcaattgcat atgaaaagaa      2100
agatttagag aaaaatattt tagagttggt gtctgatata tgagaaatat attaatttta      2160
ggaaaagtgg aattattaga agcagtaagg aacattaaat ttatatggtt agcaatattc      2220
ttttctattc ttggattgac gcaacctta attgataatt acatggaagt gattattaaa      2280 aatttggag gggttgatgg gattattatg gaccctaatg cacctaaacc tcaggctaat      2340
gaagttttgt tggcaacgtt tactggccaa tttaatcaga tgggtttgat tgtattggtc      2400
atcagcttta tgggtatgat agctgatgaa aagaagagtg gagttctggg gtttatattt      2460
acaaggccag tatctagtat acaatatatt atttcaaagc ttttggaaa ctggattatt      2520 agtatgatat gtatcttgat tggtgctggt gtttcatatt gttatactat ttatcttttt      2580
gattattatc catttattaa tttttattt tttctcttat tttatagttt gtggattctt      2640
tttattgtca gcgtaacgat attattaagt acttttataa aaagctctat ttttataggt      2700
gtgataacta tcgtaatatc aatggtattt atattattgg gcaatattaa taaacattt      2760 gcttttatttt taccaagtgg tgcacttaca ttagctgaaa gccaatttca aaatataaat      2820
tctaatttct tattgataat cgcacctgtt atttatattg ttgccttagt atatgcatct      2880
aaagtcatta tcaagaaatt ctaaggaggt atagaaatgt tatccattca aaatttaagt      2940
aaaacgtata aaggttctga taaggtgtt aagaatttat cattagaatt atatgaaggt      3000
gatatatgtg cttttattgg agcaaatggt gctgggaaaa cgacaacgat taaatcaatt      3060
gttggaatac atacatttga tcatggagaa gtgaaattgt tcaatataaa tctaaaagat      3120
aatccagagt attataaatc tttcattggt tattcaccag atacgcctga tttgtacaat      3180
aatatgacgg ggaaagcata tattgaacta atagcggcgc tttataaaat ggagaacata      3240
gaacttgaag agaaattaag ttacctaata aaagaattaa aatttgaaag tgccattat       3300 gatttggttt ctagttattc tcatggaatg aagcagaggt tagtgcttat ttcattatta      3360
```

```
atgcatgatc ctaaattaat tattttggat gaaccatttg ttggcttgga tccaaatgct   3420
attgattttt tagtgaatga aattagaaga cgagccagtg aaggagcaat tattttatac   3480
tctacacacg tacttgaagt tgctgaaaaa ttatgtaata aacttgttat tttagatcat   3540
ggtaaagctg tagtaaatga tacaatggaa agtattctta aaaaagcacc attaaatgaa   3600
atatttaagg atgtgacttc tgatgaataa tcttaaattg ttatttttat ttcgattaaa   3660
aaatcaaacg caattatcta atttgaaaag caataataaa gaagtaagaa agcattctat   3720
ttacactatc acaggatata ttactgcatt tataatgttt ttaggatata tagttttcat   3780
tgcaatagat ttaagtttaa ataataatat ccatgaattt tttgtattat aacatccat    3840 tttattttgg ctatttggta tatggaatat acttagcgga ttcgataatg tcatagaagg   3900
gaaggatggt gaatttattt atagtctgcc aataaaaaac tggcaagcaa aactgtttta   3960
tttattaagt aaatatttga ttcatattac tttgactttt accatttta ttctaagtgt    4020 tgtcttcgta atacctttgt tatctcattt attgtcagta attcttatga ttattttatt   4080
aagttttatt gttcctcttc tagctacaaa tatacctttt ataatttcca tattagtaag   4140
aaatatacta atatttatca agttacgtaa taatataaca gagtcaatt ttacattatt    4200 cgcatttata gctccgttaa tttattttat ctttaactct gaaatggttg gttataaaga   4260
atggtttata aatacatcta ttttacggta cccgcttaac aagatgacta gctctccttt   4320
tttatttaat atgttttttgt taattgttat taccttatt acaacgttca tagttattta   4380
tatgctgatt aattttcatg attcccttag aaatcaaaca aataagcgaa agaaaaaaag   4440
aaatgggaat acgtattta aaataaattc accagtattc agtttaataa taaggaatt     4500 taaattatat ttttcctctt taacttatgt tagtaataca atcataactc cagtagttat   4560
tgttatacta aatataagta ttctaattgg aataataccc agtattgatt caatttctta   4620
tgatttacta ggatttacta ttagttctca gcaaatatat gtacttattg tctttacttt   4680
tgtaattctt actactacaa cttccttgtag cattcttttt gaaggaaaga gtatttggat   4740
tatgttagtg gctcctatta atattaagaa aatagcgatt ggaaaaatat agttaatat    4800 acttttattt ttaccaggta ttgttttaac ttcattgtg ttctatacag tatttcatgc    4860
aggtatattt tatttaatta taatcagtac gttgttagta tctaccctca ctttgataag   4920
tattattggg ttttttagtaa atttacggtt cccatcctat aactggagtt ctgaaatgga   4980
agttgttaaa caaagtaaag gaactattgt aactgcaata ataagtatga taattattcc   5040
gatagttatt gcatttgttc taataaataa ctcattgctg actttattgg taattttat    5100 agaaatggca gtgattataa ttatgtttaa aaaaattaca gcagatagtt taattttaaa   5160
ataataaagt atgtaataag aaatacaatg taaatgtagt ataaaatccg caatagaata   5220
ttcttattat tagaagatta gttgacaaaa tattttattc tttatcttta gagatgtaat   5280
agacacaata aagaaaaatc aatatttaaa aaaatattcg cttaatatag ttgacatatt   5340
aattaaatag attaagataa aagtgactag aaaaatttat ttagtcataa atgaataggg   5400
gtattaatat ggcattctct aagattgaaa aagaaatat taagaaaaat ttattagaaa    5460
attgtgaaaa gcattggtca aaatacggtt ataaaaaaac aaatattaat gacttgtgcc   5520
aaatttctgg aatatcaaaa ggttcttttt ataatttttt tgattcgaag gaggcattat   5580
tttatgaagt catcataagt gcacacaata agttagtgaa aattacagag gacggtttaa   5640
aaaaatgtat gactaaatat gatttgctta attttttgaa actgttatat caggaatata   5700
caaaattaga tttttttaaat gagacatcac aacaggattt tatcaaattt ttaaataaac   5760
```

```
tagatgtaaa aaaacaaaaa aaattaatgg aaaatgtaca ctatgatctt cgtaatgaaa      5820
ttaggaaatc aaatttgaaa tataaagttg atgaaaattt agggatttct gccttaggat      5880
atatctttac tcctttatca aaagaagagt tagatatata taatgaaaat ggaacaatcg      5940
agtttttaat tgacataacc gttgatagga tttttgaata agttttagtt aaaggaggtc      6000
aatcagatgg aattaattaa atcatcctat atgacacaag cttctatgga agaagaacaa      6060
ctttatttga tatggaataa atcatctgtg actagatcgt tatatacgga aacatggtgt      6120
tttaaattac taattgaatg tgacaaaaat aaacttgtga aagcactttg tcaaatttt       6180 gaagaaaatg atattctaaa atcaaatttc atatttaaaa ataatcgtgt atataaatac      6240
gtaaatcata cgaatcctgt tgtgataact gaaaagtgaa agagacaaa tttatatcag       6300 tttataaata aatacaaaac ggaagagttt gatttaaata atgacgtcct atgtcagttt      6360 tatatttta tagataatga atgaatagc acttatctta ttataaacca ccaccacatt        6420
gtatcagatg ctcaaacaaa aaatttaata cttcgaaggt taaagagat actagatcca       6480 agtagggtta ctgaaaaaat tcatcatgaa ttatctacta attatcaaga acacttaaag      6540
ccattaaaaa agctcaaaca agataaatac atacaaaaag cacttgatat acctcgtcgt     6600
attaagcctc atagaatttc acaaactaaa tttactggct atactaagaa tttaaaacta     6660
aataatgaaa agttccaaga attagtaaca tattgtaaca taaataaaat ttcaaaatac     6720 acttttttc taactacttt ttattacact ttacttcata ttaccggtga ggattatttc      6780
agattaggta tacctttctc tactcgaaat aatagtgagg attttaaaaa atgggatat      6840 tttgtgaata tattgccttt atatattcag gatagtattt atgataaagg ttatacctgg      6900
ttagataggt ttaaacttgt tcaaaaagaa atatttaaaa catttgaata taagaatgca     6960
cgttatcggg atttaactac attctttgat tcgccattaa acagaatgca agatgtagtt     7020
tttagctacc aagaaacaga taagaatgtt tcggacattt tttatgagat taatacaaat     7080
caaacaggag caaagtttga attgactggc aacgttaaag ttttaggaaa tgaagcgttt     7140
ttggaaatcg agttctctga tgaaatattt aatgaagaag aatcgaaatt tttgattgat     7200
acttataaaa gtataattga taaagcttta aaaggtaatg attttgaaaa tagaggaagt     7260
aatgatagct taattcaagg taaaaaagtt agtctagaaa aaaataataa tcttttataaa    7320 gaatttagaa atatagcatt taacgaaaaa tataagcaca aaatagcaat tatgtcaaaa     7380
caatatcaaa ttacttatttt cgaattaaat acattggtcg ataaactagt aaatgcaatg    7440
ttaaattata aaatttctca ggatgacagg atagctattt ttttagatag aggaattaag     7500
aatattgcat taatgatagc tttagctaaa atgaatattc ctttttttaca tttaaataat    7560 aactatcctg aagaaagaat taaatatatc ttagatgatt ttaatgcaaa atatgttatt     7620
acagataatg caaatcattt aaaaataagt gagaaacaaa aagttttaga tagaaattta    7680
ttcatttatg ataatttgaa ttacaataaa actcttgtt ttagggaaga tgaaaactgt      7740
ctggaggtat tttatacatc tggtacaact ggttttccta aaggtgttaa aataactcat     7800
aaaaatgttt tcaattttac ccggaatttt gaagcatatg gtttaaatga taaggatgtc     7860
tttactcact gcagttcttt atcatttgat gcttctacat ttgaaatatg gatgtctttta    7920 cttaatggat gtagtttatt agtggttccc gatccaataa ttgatattga aaattggaat    7980
tttgaggaat tacaattaaa acctactatt tcttttttaa caacatcgtt gttttattct    8040
atgattgata atgagtcaat acaattgttc aaagatcata ggaaaatttt tattggtgga   8100
```

-continued

```
gaaaaagctt tagcaaaaca tattaaaaaa gcaattaaaa acttagagaa tgttagtatt    8160
gttaatggtt atggtccaac tgaaaatact acttttacga ctacaatgga atttaataat    8220
tcattctttt ctaacgttcc tattggaaaa cctggagtca atgtgaaaat cggcgttgta    8280
aataaaagaa atatgcttct accacataat tgcgaaggcg aaatagtaat tggtggtgaa    8340
aatcttagtt caggatactt aaatgaaaat attacaaaag aaaaatttgt gacgattgat    8400
gaagtgactg acaagttata taaaagtggt gatattggtt atatttcaag tgattcaacg    8460
cttaattata ttagcagaat agatagccaa attaaactga gaggatacag aatagagtta    8520
tctgagattg aagaaaatct acttaagcat gatttagtgt caaattgtgt tactgaagtt    8580
atcaataatt tattagtatt agtttatgaa ggtcaactaa agactaataa ggctaaagag    8640
tttttaacta atgtattgcc aaattatatg gtgccaaatc aaattattca taccgataag    8700
attccattaa cgttaaatgg caaattagat aaatcaatta tagaaaagtt ttatatagaa    8760
aacagtgata atattccggc cactaaagaa gaaaaaatga ttatggaagt aataaaaagat    8820 gccacgcata gtcaaagtgt tagtacgaaa actaatttat atgaaattgg tatagactcc    8880
attaaatcga tgcaaatttg ttctaaatta agaaataaag gttataacat tactatgagc    8940
gaatttatgg actgccaaaa tattaaaagt ttaggagaat ttttaaaaaa agaaaataat    9000
aaagaggtac gccaaaataa tcagatttgg aattcaaatg aacttagtcc aattcagaaa    9060
tggttttttg aaacacagaa agaagacata tctcattgga atcaaagtgc tttaattgaa    9120
ttaaaaaaca taaaagaaga aaaggatatt attaattgct aaaacaact tatcgaatta    9180 cacccctatat tgaaatcacg atttattta gataacggtg tctataggca agtcatagat    9240 aaagaaaat atgagataa ttcagagaaa gtacagagtt taagtgaatt taataactta    9300
ttaaatattg ggcaatcatc actaaatatt cacaaaggta tatacaattt taaaataata    9360
tattatcaaa atcaagtata tattcacttt attatacatc atttagtgat tgacggggta    9420
tcatggagaa ttatttttaaa tgatttctct gaattattag aaggtaataa taagtataat    9480
tatgaatcga gtaactttga tagttgggta aaatatataa aaaattatga agatgggcta    9540
tcagaaaatt atttttcgga atggaagaat cagattaata ataacaaaaa gtgtaaaatat    9600 aaagatttaa aagattatga catagcattg agtaaagagg aaactgaagt tataattcga    9660
ttcgcgaatc agaagaacca tggaaacatg gaggctgttc ttattgcagt tattgcacat    9720
actctaagta aaaataatat catacccaa aaatctattt tactattaga aggccatggt    9780
agaccaaaag aaaagaatga gtttattaat acaatgggct ggttcacaaa tatatatcca    9840
atgaagatag aactaaatga tgatatttaaa atatcagctc aaaagatctt tttaatcaa    9900 ataaaaatcc ctaataaagg aatcggctat caaagatatt ttgatttgaa tttttgtcat    9960
gattggagtt ttaacttttt gggtgatatg acatttaatg actatcctga gtttaagata   10020
gtagatattt tttcagaaaa tgacttttct ccaaacagtc aggctttatc aaatctgcat   10080
gtagatgtta tttaaataa tcaagaatta agtattaaat ttaaatataa taaaaaacta   10140
tataatagtt cggatttaa aaaagtggaa atggaatttc aagattcact atatttgttg   10200
aaagatgctc aaaatggtca aatatatcca attaatcgaa ctcaagaagc aatgataatg   10260
gattattatc aaaatcccaa aagtggaaat tacattattc aatgggaatc tgaaaccaaa   10320
aacttggaag tagaaaaaat cttaagtgca attagagaat tgcttcgaaa agtagaacct   10380
ttaagggtgt cttttctga gatagatgga gaatggtatc agaaggttaa tgaacttgat   10440
gattttggat taaatcagct tataaaaatt tttgactta gtaacaatag caactcaaat   10500
```

```
aatcttataa ataatctgct tataagtcaa agacacatac cgtttgatat tcagagagga   10560
ccattaataa ggtttcttat tgttaaactt gaaaatggtt ataaaataat tatggaaaat   10620
catcatttaa ttattgatgg ttggagtatg tcaacaatct ttaattattt caataaatta   10680
tatgataatg ataaaaaact cagagatatt aacattcttc aggatagatt aattagtaat   10740
actaagccaa aaaatctaga tgagtttaaa gatattttg aaaaatatga acctattaac    10800
ttacctaaga tttctaatga aggtttagag gaagaaacaa tctatataga aaaagtgat    10860 aaacattata gttttttaga aagtaacagt ttaacaccaa ataattattt tctattactc   10920
tggtctctga cattgaaata tttatttggt aagaacgata tcttgtttgg agtgacaaca   10980
tctggtagaa gtaaatttca tagtaatgag atagatggag ttggtatgtt tgtaaccact   11040
ctaccattca gaattgattt tagagattgc caaacaataa agaagattt aattccaata    11100 attaaagata aaatgaattc tattttagaa aatgatttta ttacatggaa agatataata   11160
atggaatcaa atatagataa tgaaattcag attggttatg tatttgaaaa ctatcccaaa   11220
gtacaaacaa atggaatttt ttcatttgat acttcaaaag gacatgaaca ggttaatttt   11280
ttgttggcat tatctgtgat tgatatgaaa cataattata aaatagatat aaaattagat   11340
gagaagtttg ttaataaaga catgttgcat agctgtaaaa tattgcttaa acaaattaat   11400
ctgtttttag aaaatcagat taatgaagtg agtgaaattt caaataaaatt acttagcaat   11460 acttcacttt atccgcaagt aagggttatt acggaaatta atgagactgt ttcgagtgta   11520
ttaatacaac agttttttaaa atataataat aaattgttga taaaaagcaa agaaaaagaa   11580
tacacctata atgatgtata caatattgtt cgaaatatta ttaatcgtac tgaactatca   11640
gatagtgatg tagttgcggt gatgacaaaa gatagaacaa aaatgacttt atatgcaatt   11700
gcatgtttca tatccggagc aacttatata cctataacag aggaaattaa taaaaataga   11760
attgaaatga tgattaataa tgccggagta aattgtttgt ttaatggcga tggttccttt   11820
agtcgattgg aaggtacttc aacaacttca cttgatgata tagcttatat catttataca   11880
tcaggatcgt ctgggtacc aaaaggagta aaagtttcaa agtataatct tactaacctc    11940
ttaaaagcat tggctaggga acatatagct aacgagtcag atatttggta tcaaaatata   12000
gtgatgaatt ttgatccatc catattcgat cttctaatgc ctattattag tggatgttct   12060
atgtatattc ctgagaaaag attatacgct actgaaatcg aatatttgct cgaaaaagag   12120
aaaattacaa ttttttcgat gactccttcg cttgctaaaa atttagaact gaaaaataat   12180
agcagtttga gggtaatgat tataggtgga gaaaaattaa ctaaaaatga tattgaaaat   12240
ttacccaaaa aaatagaaat aattaatatg tatggtccaa cggagtcaac tattatttcg   12300
aatatgtttc gaataaacag cgaaaatata aatgattatc tccattatcc aataggcaaa   12360
cctataagta gtttgaatgg ctttacaata tcacccgata aacaaatact gccgtttgga   12420
gttgtaggag aatatgtgtt aaaaggttct acagttactc aagggtatac agataaacat   12480
ttaaatagta atttttctgat tgaaaataac aggaaaaatc attttaatac aaaagacctt   12540
gtttatattc aatcaaatta tctaacccat tatattaatc ggttagataa tcaaattaaa   12600 cttagggggtt atagaattga gctaggagat atagaatcag cgttaaataa gataatgcct   12660
agtaactcct ataaattgat ttttagtaat aataaggatt taattttagc ttatactgcg   12720
aactacaatg aggaagaaat acacgtattt ttgaagagaa atttacctag ttatgccgtt   12780
cctaatttca tcaaatatat cgaagatttt ccgataacaa ttaatgggaa aatagatttc   12840
```

```
aaagaaattg aaagtatagt aaaaagagag ttgaatttta atatcgatat caatcaatat   12900
aatgacgata ttttagaatt tttaacacta tgctctgata cattggaaat agggaaaatc   12960
gatttaaatg ataatttctt cagtgttgga ggtgattcaa ttaaaggtat gaagctgatt   13020
agagcattaa atagggaata tggagttgaa atgaaaataa aggaattgtt taaagccagt   13080
aactttagcg aaatttattt actattaagg agggataaaa gtggtaaata aactttatga   13140
attgagtcca cagcagaaag gtatttggtc aagaatccaa caatatagag aaaataatga   13200
atacctaatt cctttagtca ttcaacttga tgaaggtata aaaaagaag atgttgaatc    13260 agcacttaat gaaattatta aaagtaattc tgctttaagg gtagaaataa tgatggggaa   13320
attcccgaaa caattgattc atgaaaaagt aaatattgaa ttaagaaata taaatttaat   13380
agataatgaa aatgattttg aatatcaaat aaaaaaatat atcgaagaac caatgtctct   13440
ataccaaaaa ttatgcgatt ttaaattatt tcaacataag aaaaaaaact ttctagtttg   13500
taaattccat cacattattt tcgatggtca ttcaggaaaa atatttaaag aagaattaga   13560
aaggcaactg tcttttaaaa aaaatatatg tataaaaaat aacactttt atgagagcta    13620 tttaaataaa gcatgtgatc aaattgtttt ggaggaagat aaaaaatatt ggaacaagat   13680
ttttaatagt gagattgatg attatttcat gattaataat aaagaaggaa acgaaaggat   13740
tgaatatgag aatgaactaa gtgtaagttt aaataattta aaagagcatt cacatcaact   13800
aaaacaaagt ttatttttcaa cactcttagg tttatttcgt ctctatgcat ctaaacattt   13860
taataaagaa acattgtcta tcgcaatacc tgtctcttct agacgttcgg aacaagatta   13920
taaaactata gggtacatta cgcaggtatt tccccatgta atgaaggtgg agaaacagaa   13980
aaattatgaa gatttacaag aatattctaa tcaattgctt tatgaacttt tagagcattc   14040
tgatctttca attattgaat tatctaattt aagcaaaagt gcttccaaga atattggaga   14100
ctattataaa tgtatatttg atattgtcga agaagaatcc tatttagata ataaagtaag   14160
aatgtggaat ttacaatcag agtacccatg gatagttaaa gttatcatta gagatcagca   14220 agtgttttg aattccaatt ttaaaaaaga acttttccca ttttggaaga ttagggattt    14280
tcatgaagga tttaacttct ttattaacaa tattattagt gaatctggaa gttatttta    14340 aaaaaatgtt ggtatgccaa taaagaatt aaataaaatt ataaatataa gtaactttgc    14400
agcttctaaa aaagacatta attataataa atcgaaatta gacgtaaaaa ccttaatgta   14460
taatacggcg ataataagtg gaagcgaaaa aatttcttat aaacaattag aagaagattc   14520
aatcaaattt tctggatta ttaggaatag gaatttgaaa gtgggggcaa aatgcctcgt    14580
ttatatgaat gatactcttg aagctgttag aattttctat tgcttacaga aaacaattg    14640 ttgttttata ccggtttcta atgacacacc tttaaataga gttaagctta taattgaaga   14700
atcaaacccg ctccttattt tttcagacat tttagatgga agtgaaacag ataaaatatt   14760
agtgagtaaa ttaaataaat gtcattgttt gagcccaaac acaataatta gaggtactga   14820
tgagaactat tcacctggca catcatatat tatatttact tctggatcaa ctgataagcc   14880
gaaaggtgta atgattactt ataagaattt gtctggatta attactcaat acaaagtttt   14940
atttgatatt caaaaggag atagagttgc tcaaatagcc agtttgaatt ttgatgctag    15000
tatatttgaa atgacattag ccttttcaac attttctgta ttgattatct ttaacaataa   15060
tggaggttat gagaacttca atcagtttat tatagataat agtattaccc attttttaat   15120
gacacctgat tattatgctc tactagactt tagtaaatgt aattcattaa aaaatataat   15180
tgttggtgga gatgaattta agtttaatga tactgtacct gaaaatgtta agatatttaa   15240
```

```
tgcctatgga ccaactgaat caacagttat gtgtttaata agttaatga caaaaaaagt   15300 aaaaacctca aacttaggta aaccaatatt aaactcagga gttattttat taaacaataa   15360
tggagagata ataaatcgtc atgttgtcgg tgaaatttgt attactggac aatcagtatt   15420
tcttggttat ttagacaaaa ataaaaatta taagctagaa aaaataacat tgaataatga   15480
ggactataca atataccgta ctggagattt agcttattat gatgaaaatt atgatataca   15540
cttctttagc aggagttcca attttgtgaa gataagaggt tatagaataa atcctaatga   15600
agtaacttct gcaataataa atcttcgtga agttaataat gcagttacac tggtattaaa   15660
tggacaactc atagcttatt atattggaga tgtagatgcg attgaaataa gaaaaaaaat   15720
aaaaaacatt cttccaaatt atatggttcc aacaactatt cataagctag atgcatttcc   15780
tatgacaatt aatgggaaaa tagatagtaa aaagttgaaa gaaataaaca ctgaaaaatg   15840
tagtctaaat agttatgaaa caaccgatag tagggataca ggatttatga atattgttat   15900
gaaagtgttt caaaataaaa aactaagtaa aaatgataac ttttatgatg ttggtgggga   15960
ttctattttg agtattaaac ttgccagtga attacaggat aatggattta atatttcttc   16020
agtagaaata atgaagtcaa atgattttaa tgaattattt caaaaaaata tacaacataa   16080
ttcaaaattt aatcaagatc ctgttttttgg aaaaatcaat ttattcccaa tgcagaaatg   16140 gttttttttct caagaatttc ataatattca tcattggaat caatcaaatg aatttgaaat   16200
atttggtcaa ttcgatgaat tagattttca aacaatttat tattcaatta gggagaaaca   16260
cgatgcaatt aggagttatt ttcaaagaat taatatggaa tattgctggt tggttaaaga   16320
aaataattta gaggattcaa aaaaagaaat tcaatatgtt gatagcagtc atttttaatat   16380 taataacata aatgaattaa aaagaaacct tcacaaaaca ataaatatttt ttgatggacc   16440 attatctgca ataaagatta tcaaaataaa tgaaacgcat tttaaggtgc tgtgggttat   16500
gcatcattta atatgtgata acattagctg gttaattta aaaagggatt tcatacgtgc   16560
aattaattgc ttgaacaata ataagaaaat aactttatat cccaaatctt cgagtataga   16620
agattgggga aaatatataa taaaacagcc tcggttttca aatgatataa attcaaataa   16680
aaattcatca aaacacaaat atgaaactaa aaaaataaat attgtagaag atgattataa   16740
aaaagttaaa gaatattatc aaaaacataa tttgtctgaa gaaaatttcc tattattact   16800
ttttgcaaag gtactgagtg aacaaatggg aagagaaaag attttgatta ataagaatt   16860 aagtggcaga aattatttgc cagaaaaata ttctcttgat caaactgtcg gttggtttac   16920
aaaaacttgt cctgttgaag tagattgtac tgtaccttat aaaagctttg tatctacaaa   16980
tatctttaac attgaaaagc aaacaagttt ttttaatgaa tattttttt cacaacctgt   17040 tagtggaccg gaaatatcat ttaacttttt aggcgaatta tcaaaagagt tagatgtaaa   17100
tgccatgcaa tcattcaatg ataggtgga gtatgatttt ccggacaaaa tagctttaa   17160 tgtattaaag agagaaaatg aatattcagt gtttattatt tatcaaagtg acatgttca   17220 atatttgaa aaaataagtg agaatttatc aagcttgata aatctttaa ctaaaatgga   17280 gagacagaat gtattcggta tctctgaaga ttctttgaaa gttttaagcg attattttta   17340
aaagaatggg gtgttaatat gaaagctata gctgcatatc ctatgactga agtgcaaaaa   17400
ggaatagcgt atgaatgtta tttaaataaa gacagagaat tttatattag tcaaatgaca   17460
atagagcttt actatgaaaa tatagagatt tataaagctg cttgggaaaa aattattgac   17520 aaaatatgaaa ccttcaaaac ggcattttat tttggagaaa tgaaagatga tgttcaggta   17580
```

```
gttaataatc atattgattt caaatgggaa gtgttaactg attacaatgg tagtatagaa    17640
agtattgaag aaaagaaag aaaaagatta tcagatataa agaaacccac acttattcgt    17700
tttaaacata ttaataataa tcagaaaaac tatttgatta ttactttcca tcatattatt    17760
ttagatggat ggagtttgtc tatagtcttg aatgatgtga atagacttta ttatcaatta    17820
tttaatgaag aaaaatcata tatttataat aatactgaat tcagtgaatt tattcaaaat    17880
aaattaactg ctaacaatga aaaatcgaat caatatttc aaaatttact tactgatttt    17940
cctggattta gtttcccttc tcttacacca atagaaaaag aaggttttga acaataaat    18000 aaaatactca ctctagatat gaaagtcatt aagaatttt gcaagaaata taaaatttcg    18060
ctatcttcac ttttagctc agtttggtct ttagttgtct cagcttatac aggtaaaagt    18120 gatatttac tgaataaaac gcattctgga cgggatagca aaaaaaaaga acaaattgtt    18180
gggttactta ttgaaaatta cccgtcacga tataaaattt acgatgatga gattcttaca    18240
gatttcattg aaaataatca tattactgat attgaaacaa gagaaaagca agaattttca    18300
atgtaccaaa caaaaaaata tttatcagat attggggtta atgaatacac aaattgtgct    18360
tttgtatatg aaaactatcc cgtaaatgaa agtaaatctt ataaaatatt aaacacattt    18420
gaaaagcagt caagcgaatt aactttatct gctggagtaa tgaatgatca agttttagta    18480 aaatgatgt tttcattaga attaataaac aaagatatag catcggcctt aatagaatcc    18540
tatacagttt tgttaagcga gtttaaaa gatgagaaac aaactatcag tgaagtgatt    18600
aataaaatta gattaagtaa ggctttcgga gaggtacttc ctgtccctaa agatattcca    18660
ttaataactc atattgagga gagagtgcaa gggaaaaatg ataacattgc attttactat    18720
aacgataatg aaataaacta taatacttta attaatgaga caaaagata ttcatcctta    18780 ttaaacgatt tagagcttc ctatggagaa acagttgcta ttgattgtga tagagctccg    18840
tatgcaatat gtttaatgct tgcattagaa cagcatggca ttccatttgt atattttagat    18900 tccaaaaata ctagtgagag aaatcgattt atacttaatg attcaaatgc atcttatctt    18960
ttctatgata aaaaaaagcc ggaatatata agtgatatta aaattcgggg aataagtatt    19020
agcagtaaaa attcattcaa ctttaaaggg tctaacgagt atttgacaaa aacaaaaga    19080 gaagattatt ttcaaataat atatacatct ggtactacgg gcaacccaaa aggaataaaa    19140
ataactacga acaatatctt tgccttgtca atcaataatg gattttacga tgttaaagaa    19200
ggagatattt ttactcaagc ttcttcatta gcatttgatg catgcttttt tgaaatttgg    19260
ttaccccttt taaataatgg gtcaattgct tttattccgg atccagtttt tgatgtacta    19320
agctggaaag aagtgctgaa taaatataat attacggcct cttggtttac ttcgagctta    19380
tttaatgtat ttattgatct agatccgtat ttattttcaa aaataagtaa tgtatttgtt    19440
ggtggtgaag cactctcaag agggcatgtt ttgaaagccc tttcagttaa ccctaatact    19500
aattttttta atggctatgg accgacagaa aatacaacat ttactacgac atataagata    19560
ccaacagatt atagtgaaag atcagcaatt tcaattggaa gcttattagc taattcgaa    19620 gcggttgttg ttgatgattc taatcgaatt gtaccgatat attctcaagg agagctattg    19680
gttcgtggga aagggttatc aaaaggttat gtggaaaaca aagttaatga taataaaaac    19740
ttcttagtag aaattaatga gcaaacttat tacagaacag gtgacattgt aagctttgat    19800
ggccagcgat tccattatat tgatagaaaa gatagccaag taaaaattaa tgggtatagg    19860
gtagaagtat tagagattga aaatagaatc aaagagataa ttggagtcaa aaatgcaaaa    19920
gttatgattg gagaagataa actgattact ctttttata caggtggtat ttcaaaaaga    19980
```

```
gaattaaaga gtactttagc taacaagttc cctagttata tgaatcctaa acttgtatat    20040
cagataaaga ccatgcctct aactcttaac ggaaaaattg ataaagataa acttttaact    20100
ataaagaatg ataatggcca agaaaattta tctgaaataa agttgtggc tccaaaattg     20160 agtgatatta ttttaaaata tacagattct aaaaatatag aaagtgatgc tagctttcat    20220
gatttgggta ttgattccat gaaaacaatc agattgaata agaattaaa caaaattttt     20280 aatttggaag tatcattaaa agagtttgtt cagtttaaaa caattaatga tgttcaagag    20340
tattatatgt acgatattga aaatgaattc aagcaatcaa acggcaaata tttaggtttt    20400
gcaacaaaca tgcaaaagtc catgtactat taccaattag agcatccgga aaatacaatg    20460
tttaatattc cttatgttag aaaaattctt aaaacagata tgaaagtttc agatttaaat    20520
aataaagtaa aacaagtaat aggtgatcac aatatattta actcagcact tattgaagat    20580
aaaaatagcg atttaatatg ggtaactcaa aagaaaaatt ttgagataga acatattttt    20640
gtgccgggac aattcgataa gaataaaatt ataacttatt taaatcattc attcaattta    20700
agtgatggct tagaacctt aataaagta actttaattg aagaaaaaag ctatatttat      20760 ttaattttg tagttcacca tattatattt gatggtatct ctctggagaa atttatctct     20820
atgatattcg acgatgaaca tttagacaat actaataact actttcaata tttgagtaca    20880
aaacaagatg aaaaaagta taaaaaggat aaagaatttt ggatggaaaa agtagttaat    20940
atagagaatt atttgcgctt ttataaaaag gaatttaatc atcaaggaga aatgcaatat    21000
tttgatattc cagaagaatt aggcgtactt atagaattgt tctcacaaaa aaataatata    21060
tcaaaattta atctttgctt gaagttatat agtcaattct tattaaacta ttttaatgaa    21120
gatgctgtat atgttggaac tccattaaat aagaggacgg aagaatataa aaatacgatt    21180
ggtttattta tagaattttt gcctgtcttg gataaaaaaa gtaacatcaa tacatttaaa    21240
gaagatgtac aaaactttaa attagaacta ttcgatttat atgatcatag tgatatagaa    21300
tttcaggata taaataacat acaagcaaca agaaataatt acgaacctat aacacaaaca    21360
acttttgcta tgcaaacttt ttctgaaaaa catagcaatg aattctatga tgatctaatt    21420
ataaaaaatc acaaatactc acagtttcca ttatcattaa ctatttatga atttacaaat    21480
tgtttgaagt tacaagttga ttatgctact gaattgttta ctagccaaga aattaaatct    21540
cttatagatt tattcttaat atggtcaaaa gaggtattac ttaaatcaga catttgtgta    21600
tcagatataa ttattagaga aactaaaaaa gaaataatac cattacctac tgaaaatcaa    21660
gaagaattta ggtttgaaca aataatatat ttagtaaatg aaaataatta cgatatacag    21720
atattagatg aaaattcaaa tgaaatacct gaaaatgaaa tagctaatgt attttttaata   21780 aaattaaaag tagaaagttc taatcaaaaa atgactgaaa atattaataa agttcataaa    21840
tgtcgttttt cagactcaag agatttaaat aaatcaatgt taaatacaag gctaaaggga    21900
tttaaaagtg gagaatcaat atttataaaa gataatgacg atcaaacatt taagatata     21960 attccgtttt taaattgtaa tatgaagaaa aataatgtaa atgaaagtag ttttaaatta    22020
aatgagctaa ttctgagtga tgttaaagaa gcatttaaaa aggtatttaa gattaaaaat    22080
ataaataatg atgattcatt tcttaaatta ggtgggatt caatcaagaa tatccagatt     22140
atctcagcct taaggaagaa aaattacgtt ttatctacaa atgatttatt aaataatcca    22200
agtgtttccc tcttaacgaa gcatttacag aaaaacataa aaaataataa tatggcggtt    22260
aattataaat atctacaaaa attcaaattg aatataatgc agcaatggtt catgaaaaaa    22320
```

```
gataaaaaga attttcatca ttttaaccaa tcatttttg  aaaacatcaa tattgatgta   22380
actaaagatg aattattaaa agcttttaaa tctctgtatt catcacatgc aatgttgcgt   22440
gctgtaattc tagaagagag aggagaatta tttaattata ttcaggaaat tgaaaattta   22500
aaatatgagc aaatatttat tgaatgtaag aacgaaaagg aattctataa taaagctaaa   22560
caagctgact tttcactgga tatatacaat ggaccaacat caaaaatatt atatttttt   22620 aataatcaaa agaattgtgt aggtgtttat tttgtttgtc atcatatgtt tgttgataca   22680
ttttcaataa atataattag aaatgaaatt aatgattttt tattgtatac aaagagagca   22740
acaggagata tttctaatac tgaacttttg aataaaaaaa tacaaaacct acctagtatt   22800
aataccataa caaatcagaa gaatttaatt tattcttcaa aatcaggagt aatttcaagg   22860
aatatttcga tagaaaatag caaatattca caagtgaatt ttcctaaaat acttgcaagc   22920
agtattatta aagaaatttt gactgatgag tctttgaaac ttgacattgc tgttgaaaag   22980
gattcaagac tttcagaatc tttaaaagat tttaatctat ccgatactgt tgggtggtac   23040
actgaaatat ataatttaga tatacaacca gctatttcag tggaagaagt atacttaata   23100
ttgcaaaaag aaagtgatta taaatttcat cataagatta atagccaagt attttttaaat  23160 gttgtaaatc ttgaagaagc ccatgaatat aatgaatttt ttatatttga agaaattcaa   23220
tcaattgctg aagaaaatat acaatcaatg ccgccaacaa taaatattat taagcagggc   23280
tcgaacttga tggtaagcgt aatgaatatc aaaaactgtg aagaacatct tttaaatgcg   23340
attcatgaat ttaattgtta tattcaaaat gtaaattatt taaggtattt tgctgattta   23400
aaagtaattg gtaacccaat tatccctttt aaagagtatg ctgaactaat taatcaaaaa   23460
gaaattgaag aaatatatcc tttgtttcca ttacaagaag aaatgctgta ttcatctgtt   23520
ggagattatt cacaaagtta tattaatgaa atttcttgga ccactaaaac taatatgtct   23580
gatattatag agtcttttc  caaagttcac cgaaaatatc aagctttgag aactaagttt   23640
tggatttcag ataatggctc agtgtatcag gtaattaaaa gttcttttga tgagttaccg   23700
attaaaatta tagatttaaa atatgtagat tcgaatgaga taattgagaa gatgaatgaa   23760
attaaagaaa gaatcattgg aaaattaaga gactttaaaa atggtgtaac tcattatctt   23820
ttaatcataa ctactccaaa taataataaa agaattgttt ggttattcaa tcatatttta   23880
ttcgatggtt ggagtttatc gattcttatt aatgaaatgt ggaataaaaa gactatactt   23940
ggaatcaatg aagtttcaaa cagggactat gtactttggc taaatcaaaa taaagaaacc   24000
atttctgagt caactgattt tcaatcacta ttaagtgaat tcaatggagt ttgtagcaat   24060
ctgtttaata acagggattt attacaaagt tctagagaag taaatagggga agttagaatt   24120 actttagaaa aagagctaac taatgaaatt tacaaatatg ccaaacataa tgatataaaa   24180
gttgctcaaa tatttaacta tctatgggga tatattatta gccatctatc taaaaaatct   24240
aaagtaactt ttggtctagt cgactctggc cgtgaaataa atgtaccaga tatagaaaat   24300
aaagttggac tatttattaa gacattgcca atactttta gcagagatga agataaaaca   24360
ataatcaatg agattaaaaa actagaagag gttaaatcta atattttgc aaatgtaata   24420 agcataagta aattaaaaca aaaacttaac attccaagtt ggcaattact ttatgatacg   24480
cttcttgtaa ttgaaaattt tccagaagtt gaagaacaac cagacagtat tcaagacttt   24540
tatgctagtg aacaatcgaa tatgccatta agtatgagtg tagggttatc aagtgatatt   24600 gttttttaaat tagtatattc cagttcactt atttcagaag aagctataga aaaaataagt   24660
agtatattta aagatttgct aaaacaagta tgctctctaa aatatgtact tagagtcaat   24720
```

```
gatttgttag tacctgatat tgagattaaa ctttcaaatg aaaatgttga cgaaatcaat    24780
tcagtaaaaa aagatacaaa taaaaataac aagatttgtg aagaagaaat tatcaatctg    24840
tgggaagaaa ttttaggtac acacagcgtt tcaactaatg atgatttctt tgaaagtggt    24900
ggcgattcgt taaagctttc taaattagta ttttattaa atgagaaaat gggattaaaa    24960
atggatgtta ttagcttctt tcaagaccca acaattcaaa acattttaaa caatgcaaac    25020
agtttaggca agcagtcaaa aaaagtaatg aagggtgatg atatagagtt acctaaattg    25080
ccctctactg aaatcttaaa agtagaaaat agtaataatc atgttttat tacaggaaca    25140 acgggattgc tagggagcga attgttatat caacaccta taaaaggatt tagtgtttat    25200
acagttatta gagcagaatg ttcaaaatca gcaagaaata gagtgttaaa acagctcaaa    25260
aaaatatcag gaaaaataga gaagctaccc ttagaaaatt tacatgtggt tgttggggat    25320 attttcaaaag aattttttcgg aatgtcacaa gaagaatatg ataaattatc aaaaacttgt    25380 tcagttatt taattgtgc tagcaacgtg aatttatgg ctccctataa ggaagcatat    25440
aagtccaatg ttattggcgt tgaaaatata atgaaatttg ccaataataa attagttaag    25500
aaggtcaacc atatatcgac attgtctgta gttggacatg attattattt aattgaaaat    25560
ttggatgagg cgccaataag ttatattaaa acgaaaatac aagcagaaaa attattgaga    25620
aaataccgta caataaggaa tggtgtacaa atttcaagag taggtcgttt aaatggtaac    25680
tctcgtaata aaatgagccc aagtaaagat ttgttttgga gattgatttt atccattgct    25740
cagattggat gttgtcctca agaattttta gaacagcaaa cagatttaac acctgtggat    25800
gaggtagcta aatgcttaat gaattcgaat gcttctcata atgaaaatca aattataaat    25860
tattttacga aatcaatgat ttcatttggt gaatgtattc gtattattga agagattatc    25920
gataaaaaaa ttagaaaagt ttcattagaa gattggatat ttgaagcaga aaattcgaag    25980
gataatcata taaaaatatt aatcccacta tttaaagaaa atatcttta tgattctgga    26040 gtaaaggcaa ttaaaaattc aagttctgaa gatataggtt atcaaattaa ctacaatata    26100
aattgcagta taagttatga ttcactttat aaatatatct ataatgcctt agaaagtgag    26160
aggttattat gacaaatatt caagttctag catttcctta tgcgtgtggc tcactagata    26220
gttattcaaa attatgccat attgatggaa tagatttaat aaagtatgaa ttaccaggta    26280
gacgttctag aatatctgag aaattggatt cattaaattc agtcatgata gaggtttgta    26340
atgtgattaa ttttaattct ccatatgtca ttttggtca tagtatgggg ggatatttag    26400
caaatgaatt atgtaggttt attgagatta ataagctcca taaacctcgg aaagtcatta    26460
ttagtgggca atgccctgtt gacaacaata tgatagcct agaagaatat aatgaactat    26520
ctttggataa tacgaaaact tatatatcat tgtttaatgg aactcctcaa gaaataatta    26580
ataataaaga actaatggaa ttctatggtg aaatatttta tcaggatatg cagtttatca    26640
atcaatataa aatgaataat agttctaaaa aggtaaagtc taatgttgaa gtttggtata    26700
gtgatcaaga tattcatgta aaagaagaaa atattatgaa atggaaggat tacgctgtaa    26760
attcatgcaa ttttaaaaag tttaaaggag atcacttttt tatcaataat atatttcaag    26820
atccgaagtt aactttcgaa ctcttgtgtt gctaattat atcttaagct tagctagaag    26880
gagagaattt tatgtctaa attgcattta aatgaattat ataaaaaata taacaatact    26940
caaaagctga tagaatcaag taaaagctt catgagttct tattggacaa tgtgaagaaa    27000
catccagata agattgcagt tagaaacaaa aaagaaagta ttacttatga acagctatac    27060
```

```
aataaaatga ttgaggtaac taacttattt gattttaata atcagccaat tgcaataatg   27120
ggatataaaa atatagatgt agttggacaa attttaggag tcttgaattc aggcaatttc   27180
tttataccaa ttaatccagc ttcgccagat gaaaggataa attatatttt agataaaaca   27240
caagcgaaag cgttcattga ctgcaagaac acctattttt tacatgataa agtaaatgtc   27300
gtcaatacta ttaaaccatt agttggggat gattcccttg cttatgtgat ttttacttcg   27360
ggaactactg gaatgccaaa aggagtcata gaatctcatt atcaagttgt gaacaccatc   27420
ttcgatttaa ttgaaagatt tgatttagat gatactgatt attttttaaa tctatcatcc   27480
ctatcatttg atttaagcat ttttgatata tttgcctcaa taattgttgg agggacattg   27540
catttagttg aagatcctag agattttaat gaaattaata tgattctttc aaaatatcca   27600
gtaacgattt ggaattccgt acctaactta atgtatcttt atttaaactc caataaagtt   27660
atagagaata aattaaaaca ttgtttacta agtggagatt ttatttcagt aggattagct   27720 aaacttttt ataagaatt acccaatgtg aatttgcata gtttaggagg agcaactgag   27780
ggtactattt ggtcaattac ttataatgtt atgaaaaatg aggtaaatca attgaaatat   27840
attccctacg ggtatccttt aaccaaccaa acgatatata tattaaataa tgaacatgat   27900
ttttgtgatg taggggaagt tggagaaatt gctattggtg gaatgggagt agcccatggg   27960
tatataaatg accagtttaa aactagtaaa tcgtttatac atcatcctag attgggatat   28020
atttatctaa ctggtgactt aggtatctat acggaacata attatattaa aatacttggt   28080
aggaagaatg atgattttaa agttaatggt tatcgattga gtttaagcga aatttccaat   28140
aagtttaata agtgtttcaa tactgaaagc cgtattcttt taacaaaaga tactcctaaa   28200
aagatgatta ttgcatatga aggcgaaatt tcgtcagata aaaatgaaat attaaaaaaa   28260
ttatctaact atttattacc ttacgaaatg cccaattatg tatttaaggt agaaagattt   28320
cctatcacaa ttaatggaaa aactgattat aataagttat ttgatatcta catggagcag   28380
cgtcacttta tacgtaagaa taaagatagt accgatgatg tgagtactga gctaagaaag   28440
atgttatctt tggaacttga tgtgacaaat attcaatcta cagatacttt gttagatttt   28500
ggagttgatt ccattcaaat gatgaggatt aagatttgga ttgaaaataa aattgggcga   28560
gaattagaaa tgattgaact gtatgaaaat aactcagtga aagagttaga aactctatta   28620
actgaaaggt gaaactataa tgctgatgat ttatatttat gaaaataaga aaagtgtatt   28680
ttctacaata gagaccaagt tacttaattt tatacaggaa gaagatttga acaaaatcgc   28740
cgctttatat tacgatagag ataaactaaa tttgctatat agtagattag tggttttgta   28800
tggaatgtat aagcttagag gtatttctcc taatgatgta aatatattaa agaaaaata   28860 cggtaaaccg tatattgaga ataataacat ttacttaat atatcacatt ctggtaaagt   28920
tgtttatgtt gcattttatg aacatggtga agtaggaatt gacgttgaag aattaaatga   28980
cgttcctaat gaaattattg aatattgctt tcatgaagaa gaaaaaaaat taatgaaaag   29040
agctaaaaaa cgtgaatata gaggcgatt ttatgatatt tggacaaaaa aagaagcata   29100
tttaaagaaa aaaggtactg gtatttcaga taatttaaaa aagtaaatg taactaaaaa   29160 atatgatttt attacttttg aatggaataa ttactattgt tcggttactg ctgacggttt   29220
aaaaacatat agtattaaaa tcattcagtt tgaggaacta attcatttt taaagtcatt   29280 ttctagttt taaatagaat ttgaactaag aggctgtttt ttaaatagga caattcattt   29340
aagttatgga agttaagtga cggatgctta acttcttttt aaattaagat gtgaatagtc   29400
ttgaacctat gagcattcta aaacacaaat tatcatatat tccatagtca aaagataatc   29460
```

```
tttttattat ctgaatttta tgtttaatta tctctataga ccgttgtaaa gtcttgaata  29520
attgattata tttcaattaa ggttattatc tgttttaatg ttctaattat tggaaggatc  29580
tttgtacaaa atagctgata aatta                                        29605
```

ANTI-INFECTIVE COMPOUND

CROSS-REFERENCE TO RELATED APPLICATIONS

This is a continuation in-part of international patent application PCT/EP2016/056358 filed on 23 Mar. 2016 and designating the U.S., which has been published in English, and which claims priority from European patent application EP 15 160 285.1 filed on 23 Mar. 2015. The entire contents of these prior applications are incorporated herein by reference.

REFERENCE TO A SEQUENCE LISTING

This application contains reference to amino acid sequences and/or nucleic acid sequences which have been submitted concurrently herewith as the sequence listing text file "5402P541USCONWO.txt", file size 40 KiloBytes (KB), created on 15 Dec. 2017. The afore-mentioned sequence listing is hereby incorporated by reference in its entirety pursuant to 37 C.F.R. § 1.52(e)(5).

FIELD OF THE INVENTION

The invention relates to a novel anti-infective compound, the use thereof for the production of a pharmaceutical composition for the treatment and/or prophylaxis of a disease, preferably an infectious disease, a pharmaceutical composition comprising said compound, and to methods of producing said compounds.

BACKGROUND OF THE INVENTION

The control and treatment of infectious diseases is one of the biggest challenges of the modern society. Nearly 40,000 men, women and children are dying every day from infectious diseases worldwide.

RELATED PRIOR ART

Among the infectious agents pathogenic bacteria are more than ever of high relevance. Bacterial infections may be treated with antibiotics, which are intended to kill the bacteria or to prevent their growth. However, antibiotic resistance threatens the infective prevention and treatment of an ever-increasing range of pathogenic bacteria. Antibiotic resistance is present in all parts of the world. It is seen as an increasingly serious threat to global public health that requires action across all sectors of science and society.

There are high proportions of antibiotic resistance in bacteria that cause common infections in all regions of the world, e.g. urinary tract infections, pneumonia, blood stream infections. A high percentage of hospital-acquired infections are caused by so-called methicillin-resistant *Staphylococcus aureus* (MRSA). MRSA is a bacterium responsible for several difficult to-treat infections in humans. MRSA is also called oxacillin-resistant *Staphylococcus aureus* (ORSA). MRSA is any strain of *Staphylococcus aureus* that has developed, through the process of natural selection, resistance to beta-lactam antibiotics, which include the penicillins, such as methicillin, dicloxacillin, nafcillin, oxacillin etc., as well as the cephalosporins. MRSA is especially troublesome in hospitals, prisons, and nursing homes, where patients with open wounds, invasive devices, and weakened immune systems have an elevated risk of a nosocomial infection in comparison to the general public. MRSA began as a hospital-acquired infection, but has developed limited endemic status and is now increasingly community-acquired.

Besides prevention measures new ways of treatment of MRSA are subject of intensive research. According to a Henry Ford Hospital study the drug of choice for treating MRSA is now believed to be vancomycin. However, several newly discovered strains of MRSA show antibiotic resistance even to vancomycin, e.g. vancomycin-resistant *Staphylococcus aureus* (VRSA), as well as against other newly developed antibiotics intended for a treatment of MRSA.

Document DE 10 2005 055 944 discloses cyclic iminopeptide derivatives intended to be used as antibacterial agents. However, such known compounds have so far not proven their worth in the clinical practice.

SUMMARY OF THE INVENTION

Against this background it is an object underlying the invention to provide a new anti infective compound effective in the treatment of infectious agents which are resistant to currently available drugs, such as methicillin-resistant *Staphylococcus aureus* (MRSA), vancomycin-resistant *Staphylococcus aureus* (VRSA) or vancomycin-resistant Enterococci (VRE).

This object is met by the provision of a compound having the following formula (I):

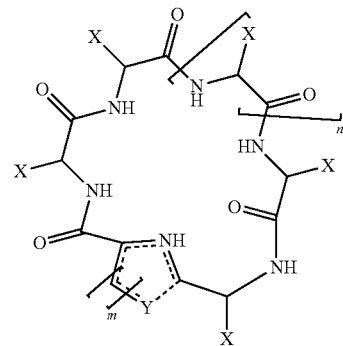

wherein

X is selected from the group consisting of: H, $CH_3$, $CH_2CH_3$, anthranylalanine, DOPA, tyrosine, threonine,

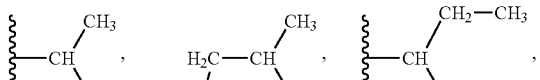

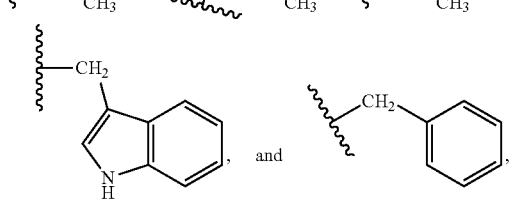

under the proviso that at least one and, preferably at most two or three, out of X is:

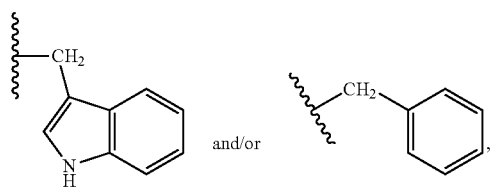 [SMILES: *Cc1c[nH]c2ccccc12 ; *Cc1ccccc1]

and/or and

Y is selected from the group consisting of O, H, OH, S, and N, under the proviso that in

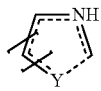

---------- represents no bond, single bond or double bond,

========== represents single bond or double bond, m is an integer between 0 and 3, n is an integer between 0 and 4, and the salts thereof, the solvates thereof and the solvates of the salts thereof.

The inventors succeeded in isolating a cyclic peptide from the bacterium *Staphylococcus lugdunensis* which falls under the scope of formula (I). This cyclic peptide exhibits strong activity against various pathogenic bacteria, including the vancomycin resistant (VRE) *Enterococcus faecalis* and *E. faecium*, *Streptococcus pneumonia*, *Listeria monocytogenes*, and *Staphylococcus aureus*. In further investigations the inventors were able to identify a core structure represented by formula (I), which is responsible for the antimicrobial activity of the isolated compound.

The new compound comprises 5-9 amino acids in a cyclic configuration. In this "large ring" among the amino acids aromatic and hydrophobic amino acids are preferred, wherein at least one tryptophan or phenylalanine is required and in an embodiment preferably at most two, three, four etc. are tryptophan or phenylalanine. In an embodiment of the invention no more than two aromatic amino acids are provided.

The new compound further may comprise a "small ring", i.e. a 5-, 6- or 7- membered heterocyclic ring, such as a a thiazolidine, oxazolidine, or imidazolidine ring. The small ring does not need a double bond, there can be, however, a single or double bond in the small ring as indicated by the dashed underlined line. Alternatively the "small ring" can be opened up without any ring structure as indicated by the dashed line.

The compound of the invention may, depending on its specific structure, exist in stereoisomeric forms (enantiomers, diastereomers). The invention therefore also encompasses the enantiomers or diastereomers and respective mixtures thereof. The stereoisomerically uniform constituents can be isolated in a known manner from such mixtures of enantiomers and/or diastereomers. If the compound of the invention may occur in tautomeric forms, the present invention encompasses all tautomeric forms.

Salts preferred for the purposes of the present invention are physiologically acceptable salts of the compound of the invention. Also encompassed, however, are salts which are themselves not suitable for pharmaceutical applications but can be used for example for the isolation or purification of the compound of the invention.

Examples of pharmaceutically acceptable salts of the compound of formula (I) include salts of inorganic bases like ammonium salts, alkali metal salts, in particular sodium or potassium salts, alkaline earth metal salts, in particular magnesium or calcium salts; salts of organic bases, in particular salts derived from cyclohexylamine, benzylamine, octylamine, ethanolamine, diethanolamine, diethylamine, triethylamine, ethylenediamine, procaine, morpholine, pyrroline, piperidine, N-ethylpiperidine, N-methylmorpholine, piperazine as the organic base; or salts with basic amino acids, in particular lysine, arginine, ornithine and histidine.

Examples of pharmaceutically acceptable salts of the compound of formula (I) also include salts of inorganic acids like hydrochlorides, hydrobromides, sulfates, phosphates or phosphonates; salts of organic acids, in particular acetates, formates, propionates, lactates, citrates, fumarates, maleates, benzoates, tartrates, malates, methanesulfonates, ethanesulfonates, toluenesulfonates or benzenesulfonates; or salts with acidic amino acids, in particular aspartate or glutamate.

Solvates for the purposes of the invention refer to those forms of the compound of the invention, which in the solid or liquid state form a complex by coordination with solvent molecules. Hydrates are a specific form of solvates in which the coordination takes place with water.

The compound of the invention may also be complexed, e.g. with iron, calcium, etc., in which the compound may act as a ligand, so that a corresponding complex is also subject of the present invention.

The problem underlying the invention is herewith completely solved.

According to another embodiment of the invention the compound is characterized by the following formula (II):

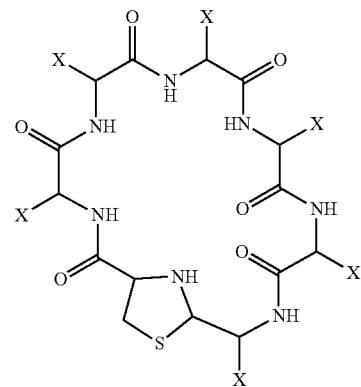

wherein

X is selected from the group consisting of: H, CH$_3$, CH$_2$CH$_3$, anthranylalanine, DOPA, tyrosine, threonine,

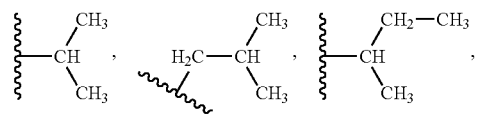

-continued

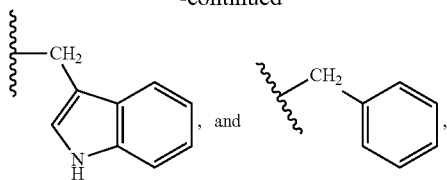, and under the proviso that at least one and, preferably at most two or three, out of X is:

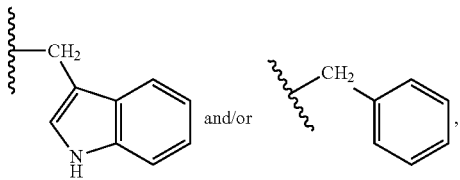 [SMILES: *Cc1c[nH]c2ccccc12 ; *Cc1ccccc1] and/or and the salts thereof, the solvates thereof and the solvates of the salts thereof.

As the inventors were able to demonstrate, the compound according to the invention consisting of a 7 amino acids comprising large ring and a thiazolidin small ring has particularly strong antimicrobial activities.

The features, characteristics and advantages specified for the compound represented by formula (I) apply to the compound represented by formula (II) as well.

According to another embodiment the compound according to the invention is characterized by the following formula (III):

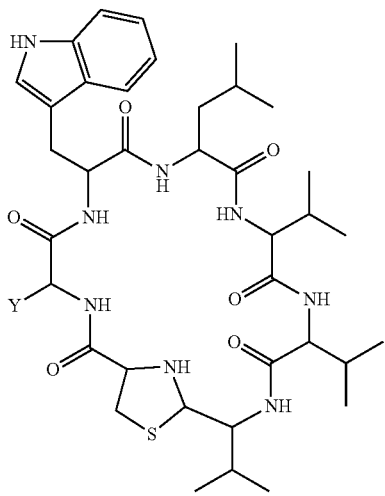

wherein
Y is selected from the group consisting of:

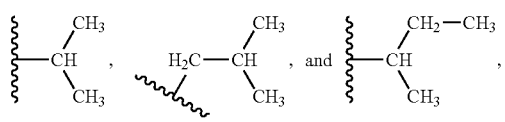

As the inventors were able to realize the compound according to the invention represented by the core structure of formula (III) exhibits a very high antimicrobial activity.

The features, characteristics and advantages specified for the compound represented by formulas (I) and (II) apply to the compound represented by formula (III) as well.

In another embodiment the compound according to the invention is characterized by the following formula (IV):

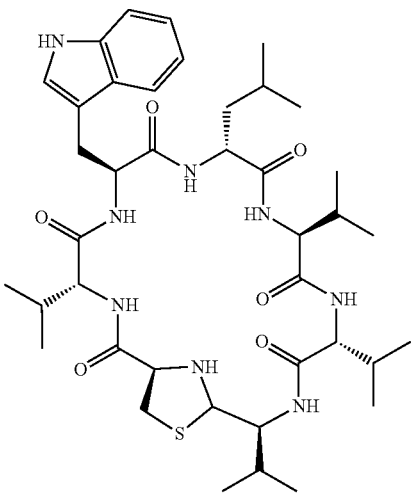 [SMILES: CC(C)C[C@H]1NC(=O)[C@H](Cc2c[nH]c3ccccc23)NC(=O)[C@@H](C(C)C)NC(=O)[C@@H]2CSC(N2)[C@H](C(C)C)NC(=O)[C@@H](C(C)C)NC(=O)[C@H](C(C)C)NC1=O]

In this embodiment the exact compound is provided that was isolated by the inventors from *Staphylococcus lugdunensis*. This compound has been exemplarily used in the embodiments to demonstrate the antimicrobial activity of compounds represented by the general formulas (I)-(III). As this has been demonstrated by the inventors, the compound has bactericidal activity, therefore ensures an effective combating of a bacterial infection. This compound can either be isolated from *Staphylococcus lugdunensis* by well-known methods of microbiology in combination with chemical chromatography or synthesized by means of peptide synthesis.

The features, characteristics and advantages specified for the compound represented by formulas (I), (II), and (III) apply to the compound represented by formula (IV) as well.

In another embodiment of the invention the compound according to the invention is provided for the treatment and/or prophylaxis of disease, preferably an infectious disease, further preferably a bacterial disease, further preferably an infection by a Gram-positive bacterium, highly preferably an infection by *Staphylococcus aureus*, especially including its methicillin-resistant (MRSA) and vancomycin-resistant *Staphylococcus aureus* (VRSA) forms.

This measure has the advantage that a compound is provided being effective against a broad range of infectious agents and in particular against *Staphylococcus aureus* in its MRSA variant, which is responsible for several serious infections in humans.

Due to its pharmacological properties the compound of the invention can be used alone or in combination with other agents for the treatment and/or prophylaxis of diseases or infectious diseases, respectively, in particularly bacterial infections.

For example, local and/or systemic diseases can be treated and/or prevented, which are caused by the following pathogens or by mixtures of the following pathogens:

Gram-positive cocci, such as Staphylococci (*Staph. aureus, Staph. epidermidis*) and *Streptococcus* (*Strept. agalactiae, Enterococcus faecalis, Strept. pneumonia, Strept. pyogenes*), Gram-positive rods, such as *Bacillus* (*anthracis*),

*Listeria* (*monocytogenes*) and *Corynebacterium* (*diphteriae*), Gram-negative cocci (*Neisseria gonorrhoeae*) and Gram-negative rods, such as Enterobacteriaceae, e.g. *Escherichia coli, Haemophilus influenzae, Citrobacter* (*Citrob. freundii, Citrob. divernis*), *Salmonella* and *Shigella*, further *Klebsiella* (*Klebs. pneumoniae, Klebs. oxytoca*), *Enterobacter* (*Ent. aerogenes, Pantoea agglomerans*), *Hafnia, Serratia* (*Serr. marcescens*), *Proteus* (*Pr. mirabilis, Pr. rettgeri, Pr. vulgaris*), *Providencia, Yersinia*, and the genus *Acinetobacter*. In addition, the antibacterial spectrum includes the genus of *Pseudomonas* (*Ps. aeruginosa* and *Ps. maltophilia*) and strictly anaerobic bacteria such as *Bacteroides fragilis*, representatives of the genus of *Peptococcus, Peptostreptococcus* and the genus *Clostridium*; also mycoplasms (*M. pneumoniae, M. hominis, M. urealyticum*), and mycobacteria, for example *Mycobacterium tuberculosis*.

The above list of pathogens is merely to be illustrative and not limiting.

Diseases caused by the pathogens mentioned or by mixed infections which can be cured, prevented, or attenuated by the compound according to the invention are, for example:

Infectious diseases in humans such as septic infections, bone and joint infections, skin infections, postoperative wound infections, abscesses, cellulitis, wound infections, infected burns, burns, infections of the mouth, infections after dental surgery, septic arthritis, mastitis, tonsillitis, urogenital infections and eye infections.

Another embodiment of the invention relates to the use of the compound according to the invention for the treatment and/or prophylaxis of nasal colonization and infections.

According to the findings of the inventors herewith the compound is put into place at the natural environment of action of the isolated cyclic peptide.

Bacterial infections cannot only be treated or prevented in humans but also in animals. Examples are:

Pig: coli diarrhea, enterotoxemia, sepsis, dysentery, salmonellosis, metritis-mastitis-agalactiae syndrome, mastitis;

Ruminants (cattle, sheep, goats): diarrhea, sepsis, bronchopneumonia, salmonellosis, pasteurellosis, mycoplasmosis and genital infections;

Horse: bronchopneumonia, puerperal and post puerperal infections, salmonellosis;

Dog and cat: bronchopneumonia, diarrhea, dermatitis, otitis, urinary tract infections, prostatitis;

Poultry (chicken, turkey, quail, pigeons, aviary birds and others): mycoplasmosis, *E. coli* infections, chronic airway disease, salmonellosis, pasteurellosis, psittacosis.

Similarly, bacterial diseases can be treated in the breeding and keeping of utility and ornamental fish but also humans, wherein the antibacterial spectrum of the pathogens mentioned above further extends to pathogens such as *Pasteurella, Brucella, Campylobacter, Listeria, Erysipelothris*, Corynebacteria, *Borrelia, Treponema, Nocardia, Rikettsia, Yersinia*.

With the compound according to the invention bacterial infections cannot only be treated or prevented in humans or animals but also plants.

The compound according to the invention can act systemically and/or locally. For this purpose, it can be administered in a suitable manner, such as oral, parenteral, pulmonary, nasal, sublingual, lingual, buccal, rectal, dermal, transdermal, conjunctival, otic or associated with an implant or stent.

A topical application is especially preferred since the inventors successfully demonstrated that the compound according to the invention is able to penetrate even deeper tissue areas.

Against this background, another subject-matter of the invention is the use of the compound according to the invention for the production of a pharmaceutical composition for the treatment and/or prophylaxis of a disease, preferably an infectious disease, further preferably a bacterial disease, further preferably an infection by a Gram-positive bacterium, highly preferably an infection by *Staphylococcus aureus*, including its methicillin-resistant form (MRSA).

Another subject-matter of the present invention is a pharmaceutical composition comprising the compound according to the invention and a pharmaceutical acceptable carrier.

For this purpose, a "pharmaceutically acceptable carrier" is understood to mean any excipient, additive, or vehicle that is typically used in the field of the treatment of infectious diseases and which simplifies or enables the administration of the compound according to the invention to a living being, and/or improves its stability and/or activity. The pharmaceutical composition can also incorporate binding agents, diluting agents or lubricants. The selection of a pharmaceutical carrier or other additives can be made on the basis of the intended administration route and standard pharmaceutical practice. As pharmaceutical acceptable carrier use can be made of solvents, extenders, or other liquid binding media such as dispersing or suspending agents, surfactant, isotonic agents, spreaders or emulsifiers, preservatives, encapsulating agents, solid binding media, depending upon what is best suited for the respective dose regime and is likewise compatible with the compound according to the invention. An overview of such additional ingredients can be found in, for example, Rowe (Ed.) et al.: Handbook of Pharmaceutical Excipients, $7^{th}$ edition, 2012, Pharmaceutical Press.

According to another embodiment of the invention the pharmaceutical composition is provided for the treatment and/or prophylaxis of a disease, preferably an infectious disease, further preferably a bacterial disease, further preferably an infection by a Gram-positive bacterium, highly preferably an infection by *Staphylococcus aureus* including its methicillin resistant forms (MRSA).

The features, characteristics, advantages and embodiments of the compound according to the invention likewise apply to the use and the pharmaceutical composition according to the invention.

Another subject-matter of the present invention is a method of producing the compound according to the invention, comprising the following steps: 1. Providing bacteria of the species of *Staphylococcus lugdunensis*, 2. Purifying the compound according to the invention from said bacteria.

Herewith a method is provided, which has been used by the inventors for producing or isolating the compound according to the invention. The species of *Staphylococcus lugdunensis* referred to in this embodiments or elsewhere in the disclosure includes the isolate or strain IVK28, respectively.

In an embodiment of the method according to the invention after step (1) and before step (2) the bacteria and the medium of the bacterial culture are extracted and the bacterial and the medium extract are subjected to step (2) where the compound is purified from said bacterial and medium extract.

This measure has the advantage that only the main sources of the compound according to the invention are provided to the purifying step from which it can then be isolated by methods of microbiology in combination with chemical chromatography, which are well known to the skilled person.

In another embodiment of the method according to the invention in step (2) the purification involves the use of high performance liquid chromatography (HPLC) to identify a peak signal, which is associated with said compound.

This measure has the advantage that a well-established tool of peptide purification is used, which allows a reliable identification of the compound according to the invention.

In another embodiment of the method according to the invention said signal peak corresponds to a molecular mass of approx. 650 Da-950 Da, preferably of approx. 700 Da-850 Da, further preferably of approx. 750 Da-800 Da, further preferably of approx. 770 Da-790 Da, and highly preferably of approx. 782.5 Da.

This measure has the advantage that the compound according to the invention, which falls within the indicated ranges, can be easily identified via its molecular mass.

Another subject-matter of the present invention is a method of producing the compound according to the invention, which comprises the following steps: 1. Expressing the non-ribosomal peptide synthetase system II of the species of *Staphylococcus lugdunensis* (NRPS-II) in a biological system, 2. Incubating the expressed NRPS-II under conditions allowing the synthesis of the compound according to the invention, 3. Purifying said compound.

The inventors were able to find out that the NRPS-II of the species of *Staphylococcus lugdunensis* is responsible for the synthesis of the compound according to the invention and, therefore, this method makes use of the natural apparatus for producing the new compound.

In an embodiment of the method according to the invention said NRPS-II is encoded by a nucleic acid molecule comprising any of the coding sequences of the genes lugA, lugB, lugC, lugD, and, optionally, of a transcriptional regulator of GntR family, ABC transporter (GdmF type multidrug transport system), ABC-2 type transport system permease protein, ABC transporter, hyp. membrane protein, TetR/AcrR family regulator, thioesterase family protein, 4'-phosphopantetheinyltransferase, and put. negative regulator of sigY (in *Bacillus*).

The inventors were able to identify the genes responsible for the synthesis of the compound according to the invention and the optional co-factors, and, therefore, provide a method where the essential features are used in a molecular biological artificial system to generate the compounds in a large scale.

The coding sequences comprised by the NRPS-II can be taken from SEQ ID NO: 1; the nucleotide positions are indicated in the following:
  lugA: 6007-13131
  lugB: 13121-17341
  lugC: 17359-26172
  lugD: 26893-28632
  transcriptional regulator of GntR family: 427-936
  ABC transporter (GdmF type multidrug transport system): 1253-2143
  ABC-2 type transport system permease protein: 2140-2904
  ABC transporter: 2917-3630
  hyp. membrane protein: 3623-5164
  TetR/AcrR family regulator: 5409-5981
  Thioesterase family protein: 26169-26855
  4'-phosphopantetheinyltransferase: 28640-29293
  put. negative regulator of sigY (in *Bacillus*): 1027-1266

Against this background, another subject-matter of the present invention is a nucleic acid molecule comprising the nucleotide sequence of SEQ ID NO: 1 and/or any of the before-listed coding sequences of the non-ribosomal peptide synthetase system II of the species of *Staphylococcus lugdunensis* (NRPS-II). Examples for such nucleic acid molecules include vectors or plasmids configured for a controlled expression of the encoded proteins in common molecular biological expression systems. Subject of the invention is also a nucleic acid molecule encoding the identical protein and/or peptide as encoded by the before mentioned nucleic acid molecule, however having a modified or different nucleotide sequence due to the degeneration of the genetic code.

Another subject-matter of the invention relates to the products generated by the expression of the nucleic acid molecule according to the invention, including proteins and/or peptides encoded by any of the genes lugA, lugB, lugC, lugD, transcriptional regulator of GntR family, ABC transporter (GdmF type multidrug transport system), ABC-2 type transport system permease protein, ABC transporter, hyp. membrane protein, TetR/AcrR family regulator, thioesterase family protein, 4'-phosphopantetheinyl-transferase, and put. negative regulator of sigY (in *Bacillus*), or encoded by before mentioned nucleotide sequence which are itself subject-matter of the present invention.

A further subject-matter of the invention relates to an antibody specifically directed against any of the products (peptides, proteins) generated by the expression of the nucleic acid molecules according to the invention.

In another embodiment of the method according to the invention the conditions allowing the synthesis of the compound according to the invention comprise amino acids, thioesterase, and buffer.

By this measure the conditions are adjusted in a way, which ensures a high yield of the compound according to the invention.

Another object of the present invention is a method for the treatment and/or prophylaxis of diseases, especially of the aforementioned diseases, in a living being, such a human or animal being, comprising the administration to said living being of an antibacterially effective amount of the compound according to the invention.

Another object of the invention is a probiotic comprising a micoorganism capable of producing the compound according to the invention.

The inventors have surprisingly realized that a micoorganism, such as a bacterium, producing the novel antibacterial compound can be directly used, e.g. to prevent or reduce the growing or colonization by a pathogenic microorganism of an organ of a living being.

According to the invention, a "probiotic" is to be understood as a microorganism which provides health benefits to a living being, such as a human being, when consumed or administered. In particular, the administration of the probiotic to an organ susceptible of being colonized by a pathogen microorganism, such as *Staphylococcus aureus*, will result in a displacement of such pathogenic agent. This results in a reduction of the pathogenic burden or even in a complete elimination.

In another embodiment the microorganism is *Staphylococcus lugdunensis*. *Staphylococcus lugdunensis* can be used in its natural form, i.e. as the wild type, or as a modified form, e.g. a genetically modified form or an attenuated wild type variant, however still producing the compound according to the invention.

In another embodiment of the invention the probiotic is used for preventing or reducing the colonization by a pathogenic microorganism of an organ of a living being, e.g. a human being. The organ may be the nose, wherein the probiotic may then be administered into the nose of the living being, or it may be the skin, wherein the probiotic may then be administered onto the skin of the living being.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention.

The features mentioned in the specific embodiments are also features of the invention in general, which are not only applicable in the respective embodiment but also in an isolated manner in the context of any embodiment of the invention.

The invention is also described and explained in further detail by referring to the following drawings

BRIEF DESCRIPTION OF THE DRAWINGS

FIG. 3A shows HPLC-UV chromatogram ($UV_{210\ nm}$) of cell extracts of *S. lugdunensis* wild type (blue) and mutant M1 (red) (x-axis: time [min], y-axis adsorption at 210 nm [mAU]; FIG. 3B shows HPLC-MS of the peak at 10.6 min retention time resulting in a mass of 782.5 Da (ESI pos.: m/z 783.6 [M+H]$^+$, ESI neg.: m/z 781.5 [M-H]$^-$, m/z 817.5 [M+Cl]$^-$);

FIG. 6A shows a killing curve. Incubation of *S. aureus* with a 10×MIC of lugdunin leads to complete killing of the inoculum after 30 h. Data represent medians ±S.D. of three independent experiments. FIG. 6B shows serial passaging of *S. aureus* with sub-inhibitory concentrations of rifampicin leads to rapidly increasing spontaneous resistance against rifampicin. However, such resistance development was not observed with lugdunin. A representative of two independent experiments is shown.

FIG. 8: shows that lugdunin is active in vivo in a mouse tape-stripping model. After colonization of shaved C57BL/6 mouse skin with *S. aureus* Newman lugdunin was applied three times in a few hours distance. After 45 hours mice were sacrificed and the numbers of bacteria were determined on the skin surface (wash fraction) and in the deeper skin tissue (scrape fraction). Treatment with lugdunin significantly reduced the bacterial load in both fractions indicating its efficacy also in vivo. (*$p<0.05$);

FIGS. 10A to 10E show that Lugdunin-producing *S. lugdunensis* eradicates *S. aureus* in vitro and in vivo in cotton rats. FIG. 10A shows *S. aureus* is overgrown by *S. lugdunensis* IVK28 wild type on agar plates inoculated at ratios of ~90:10. In contrast, FIG. 10B shows IVK28 ΔlugD is overgrown by *S. aureus* at ratios of ~90:10 (b). FIG. 10C shows the capacity of *S. lugdunensis* ΔlugD to overgrow *S. aureus* is largely restored by plasmid-encoded lugD. FIG. 10D shows *S. aureus* overgrows IVK28 ΔlugD even when inoculated in ratios of ~10:90. Data represent mean values ±S.D. of three independent experiments. Significant differences between starting conditions and indicated time points were analysed by one-way ANOVA (*, $p<0.05$; , $p<0.01$; *, $p<0.001$; ****, $p<0.0001$; n.s, not significant). FIG. 10E shows cotton rat noses co-colonised by *S. aureus* and *S. lugdunensis* IVK28 wild type show significantly less *S. aureus* CFUs after five days compared to *S. lugdunensis* IVK28 ΔlugD. Horizontal lines represent the median of each group. Significant differences, calculated by the Mann Whitney test, are indicated (*, $p<0.05$).

DESCRIPTION OF PREFERRED EMBODIMENTS

A. Methods

1. Strains and Growth Conditions

Figure 1:
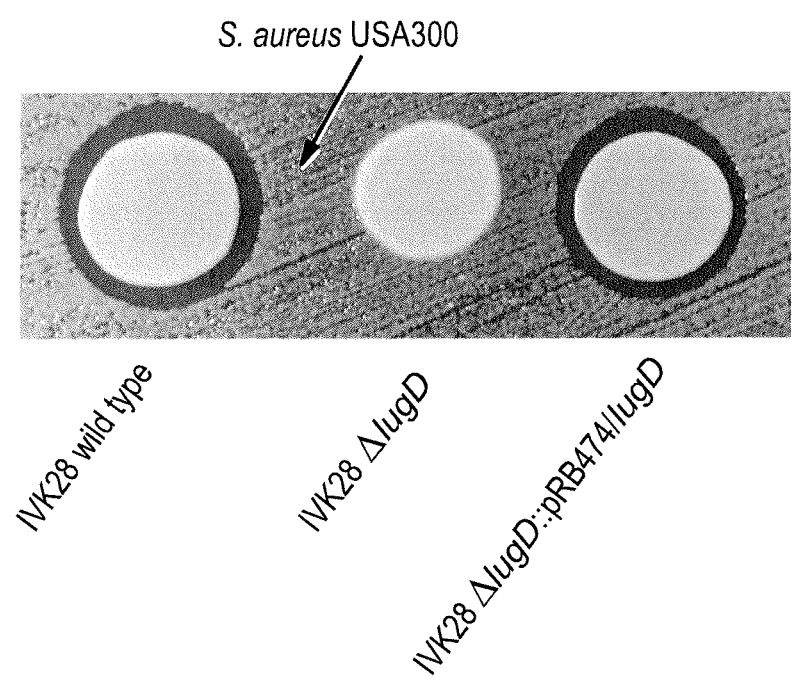
FIG. 1 shows the lugdunin production by *S. lugdunensis* wild type and isogenic mutants. Bioactivity assay with the *S. lugdunensis* IVK28 wild type, the ΔlugD mutant and the complemented mutant against *S. aureus* USA300. BM plates were inoculated with a lawn of *S. aureus* USA300. Hereon *S. lugdunensis* IVK28 cells from overnight cultures of the wild type, the mutant ΔlugD and the complemented mutant ΔlugD::pRB474/lugD were spotted.

The *Staphylococcus* strains used in this study were *S. aureus* USA300 LAC, *S. aureus* USA300 NRS384, *S. aureus* Mu50, *S. aureus* RN4220, *S. aureus* SA113, *S. aureus* Newman, *S. aureus* PS187, *S. lugdunensis* IVK28, *S. lugdunensis* IVK28 ΔlugD, *S. lugdunensis* IVK28 ΔlugD::pRB474/lugD, and *S. lugdunensis* IVK28-Xyl. Further strains used for MIC determination were *Enterococcus faecium* BK463, *E. faecalis* VRE366, *Listeria monocytogenes* ATCC19118, *Streptococcus pneumoniae* ATCC49619, *Pseudomonas aeruginosa* PAO1, and *Escherichia coli* DH5α. *E. coli* DC10B was used as the cloning host. In addition, a set of 60 *S. aureus* and 17 *S. lugdunensis* strains were isolated from diagnostic samples in the course of the colonisation study described below.

Basic medium (BM: 1% soy peptone, 0.5% yeast extract, 0.5% NaCl, 0.1% glucose and 0.1% $K_2HPO_4$, pH 7.2) was used as the standard growth medium. MIC determinations and killing assays were performed in Mueller Hinton Broth (MHB; Roth, Karlsruhe, Germany). For the identification of *S. lugdunensis*, selective *S. lugdunensis* medium (SSL) was used as previously described in the art. When necessary, antibiotics were used at concentrations of 250 µg/mL for streptomycin, 10 µg/mL for chloramphenicol, 2.5 µg/mL for erythromycin and 100 µg/mL for ampicillin.

2. Bioactivity Test

The anti-*S. aureus* activity of *S. lugdunensis* IVK28 was identified by screening 90 nasal staphylococcal isolates for the capacity to inhibit growth of *S. aureus*. For this purpose BM agar was inoculated 1:10,000 with an overnight culture of *S. aureus* USA300 LAC. The test strains were inoculated on the resulting bacterial lawn, and the plates were incubated for 24-48 h at 37° C. To investigate the production of antimicrobial activity by IVK28 under iron-limiting conditions, BM agar was supplemented with 200 µM 2,2'-bipyridine.

3. Transposon Mutagenesis and Elucidation of the Lugdunin Gene Cluster

The temperature-sensitive plasmid pTV1ts, which contains the 5.3-kb transposon Tn917 ($erm^R$) from *E. faecalis*, was transferred into *S. lugdunensis* IVK28 by electroporation. Transposition mutants were screened for loss of antimicrobial activity against *S. aureus*. Chromosomal DNA was isolated by standard procedures from non-inhibitory clones, and the primers Tn917 up and Tn917 down (Extended Table 2) were used to directly sequence the flanking regions of the transposon insertion site. Sequence analysis was performed with DNASTAR Lasergene software (DNASTAR Inc., Madison, Wis., USA). Bioinformatic analysis was performed by BLAST® and antiSMASH 3.0.

4. Generation of *S. lugdunensis* IVK28-Xyl

The flanking regions of lugR were amplified by PCR with the primer pairs SlPr1-up/SlPr1-down and SlPr2-up/SlPr2-down. The plasmid pBASE6-erm/lox 1, a derivative of pBASE6, already containing an erythromycin resistance cassette in the singular SmaI site, was linearized with Acc65I. The identically digested SlPr1 PCR product, containing one natural Acc65I restriction site and one introduced by the primer, was ligated into pBASE6-erm/lox1.The resulting vector with the correctly oriented SlPr1 PCR product and the SlPr2 PCR product were ligated after digestion with EcoRV and BglII. The resulting pBASE6-erm/lox 1 construct with both flanking regions inserted was linearized with BssHII, treated with Klenow enzyme and digested with BglII. The required xylR fragment with the downstream-located xylAB-promoter was excised from pTX15 by HindIII restriction treatment with Klenow enzyme and subsequent digestion with BamHI. The ligation of the xylR fragment into the appropriate vector generated pBASE6-erm/lox1-xylR, which was transferred into *E. coli* DC10B and subsequently into *S. aureus* PS187. The resulting plasmid pBASE6-erm/lox1-xylR was transduced into *S. lugdunensis* IVK28 via the bacteriophage Φ187. Homologous recombination for replacement of lugR by erm/xylR was performed, as previously described in the art, generating the xylose-inducible lugdunin producer strain *S. lugdunensis* IVK28-Xyl.

5. Production and Purification of Lugdunin

A fresh overnight culture of *S. lugdunensis* IVK28-Xyl was inoculated 1:1,000 in BM without glucose and was supplemented with 0.5% xylose. After incubation at 37° C. under continuous shaking (160 rpm) for 24 h, whole cultures were extracted with 1-butanol at a ratio of 5:1. The aqueous phase was discarded, and the organic phase was evaporated at 37° C. under reduced pressure and finally dissolved in methanol. The methanol extract was applied to a gel filtration column (Sephadex LH20, 1.6×80 cm, flow rate 1 mL/min). The active fractions containing lugdunin were pooled, evaporated at 37° C. under reduced pressure and dissolved in dimethyl sulfoxide (DMSO). This solution was then subjected to a preparative reverse-phase HPLC column (Kromasil C18, 7 µm, 250×20 mm; Dr. Maisch, Ammerbuch, Germany) with an isocratic elution at 79% methanol in water for 20 min. The peak containing lugdunin was baseline-separated from the remaining compounds, and methanol was evaporated at 37° C. under reduced pressure to yield a white powder of pure lugdunin.

6. Chemical Synthesis of Lugdunin and Lugdunin Derivatives

Total chemical synthesis was achieved by Fmoc (9-fluorenylmethoxycarbonyl) strategy based manual solid-phase peptide synthesis and was established on an H-Val-H NovaSyn® TG resin (Novabiochem, Switzerland). Amino acids were coupled in a four-fold excess using HATU (1-[Bis(dimethylamino)methylene]-1H-1,2,3-triazolo[4,5-b]pyridinium 3-oxid hexafluorophosphate). Valine positions were coupled twice by use of PyOxim ([Ethyl cyano(hydroxyimino)acetato-$O^2$]tri-1-pyrrolidinylphosphonium hexafluorophosphate) for the second coupling instead of HATU. Peptides were cleaved from the resin with acetonitrile/water/trifluoroacetic acid (79.95/20/0.05) for 30 min. Lyophylization overnight yielded the crude product. Crude synthetic lugdunin products were purified by RP-HPLC and compared with the natural product by HR-LC-ESI-MS, additional chiral-HPLC methods (column: Dr. Maisch Reprosil Chiral NR, Ammerbuch, Germany; elution with 80% premixed methanol in $H_2O$ at 1.5 mL/min flow rate), bioactivity assay and advanced Marfey's analysis.

7. MIC Assay and Spectrum of Activity

*S. aureus* RN4220, *S. aureus* USA300 (LAC), *S. aureus* USA300 (NRS384), *S. aureus* SA113, *S. aureus* Mu50, *E. coli* DH5α and *P. aeruginosa* PAO1 were grown overnight in MHB. *E. faecalis* VRE366, *E. faecium* BK463, *S. pneumoniae*, and *L. monocytogenes* were grown in tryptic soy broth (TSB: Difco Laboratories, Augsburg, Germany). All strains were incubated at 37° C. under continuous shaking. Early log-phase grown bacteria were adjusted in MHB to $1×10^6$ cells/well in microtiter plates (MTP), mixed with varying concentrations of the antibiotic and incubated at 37° C. for 24 h under continuous shaking. The $OD_{600}$ of each well was measured with a microplate reader, and the lowest peptide concentrations, which displayed no bacterial growth, were defined as the MIC. The assays were performed in 96-well microtiter plates.

8. Killing Assay

Fresh MHB was inoculated 1:10,000 with an overnight culture of *S. aureus* USA300 LAC and was incubated at 37° C. under continuous shaking (160 rpm) until bacteria were grown to $1×10^6$ cells/mL. Then, 10×MIC lugdunin was added. At the time points 0 h, 2 h, 4 h, 8 h, 24 h and 30 h, samples were taken and centrifuged. The pellet was resuspended in 1×PBS and serially diluted. The dilutions were spotted on tryptic soy agar, and colony counts were determined after overnight incubation at 37° C. To determine cell numbers <$10^2$ cells/mL, whole cultures of 1 mL were centrifuged and plated on TSA.

9. Cytotoxity Against Human Neutrophil Granulocytes

Human neutrophil granulocytes were freshly isolated from the blood of healthy volunteers by standard Histopaque/Ficoll centrifugation. The lysis of neutrophil granulocytes was monitored by the release of the enzyme lactate dehydrogenase (LDH). Lugdunin was added at final concentrations of 50, 25 and 12.5 µg/mL in 0.5% DMSO to wells of a 96 well tissue culturing plate containing $1×10^6$ neutrophil granulocytes per well in 200 µL RPMI-1640 medium (2 g/l $NaHCO_3$, 10% foetal calf serum, 1% L-glutamine and 1% penicillin-streptomycin, PAN Biotech) without phenol red. The plates were incubated at 37° C. and 5% $CO_2$ for 3 h and the lysis was determined with a Cytotoxicity Detection Kit (Roche Applied Sciences, Mannheim, Germany). As a positive control for high cytotoxicity, 2% Triton X-100 was added to the samples.

10. Resistance Development Study

MIC assays for the antibiotics used in this study were performed as described above. The inventors determined 1×MICs of 0.01 µg/mL rifampicin and 1.5 µg/mL lugdunin against *S. aureus* USA300. Fresh MHB was inoculated 1:10,000 with an overnight culture of *S. aureus* USA300 LAC and was incubated at 37° C. under continuous shaking. Cells were grown to early log phase, adjusted to $1×10^6$ cells/mL, and dispensed into 96-well MTPs with 100 µL per well. Lugdunin and rifampicin were added at concentrations of 0.25×MIC, 0.5×MIC, 1×MIC, 1.5×MIC, 2×MIC and 4×MIC. After 24 h incubation at 37° C. under continuous shaking, growth was determined with a microplate reader at an $OD_{600}$ and cells from the second highest concentration of 0.25×MIC, 0.5×MIC, 1×MIC, 1.5×MIC, 2×MIC and 4×MIC from the appropriate antibiotic.

11. Statistical Analyses

Statistical analysis was performed by using GraphPad Prism (GraphPad Software, Inc., La Jolla, USA; version 5.04). Statistically significant differences were calculated by using appropriate statistical methods as indicated. For the human study, risk of nasal colonisation with *S. aureus* under the presence and absence of *S. lugdunensis*, as well as the respective point estimates of the risk ratio and confidence intervals, were determined using Stata version 12.0 (Stat Corp., College Station, Tex., USA). P values of ≤0.05 were considered significant.

12. Animal Models and Ethics Statement

All animal experiments were conducted in strict accordance with the German regulations of the Gesellschaft für Versuchstierkunde/Society for Laboratory Animal Science (GV-SOLAS) and the European Health Law of the Federation of Laboratory Animal Science Associations (FELASA) in accordance with German laws after approval (protocol HT1/12 for mouse skin infection and T1/10 for cotton rat colonisation) by the local authorities (Regierungspraesidium Tuebingen). All, animal and human studies, were carried out at the University Hospital, Tuebingen, and conformed to institutional animal care and use policies. No randomization or blinding was necessary for the animal infection/colonisation models, and no samples were excluded. Animal studies were performed with female C57BL/6 mice, 6-8 weeks old and cotton rats of both genders, 8-10 weeks old, respectively. The human nasal colonization study was approved by the ethics committee of the medical faculty of the University Hospital Tuebingen (project number 577/2015A).

13. Skin Infection of C57BL/6 Mice

A streptomycin-resistant *S. aureus* Newman strain was used to infect C57BL/6 mice epicutaneously by the tape stripping technique. TSB with 500 µg/mL streptomycin was inoculated 1:10,000 with a fresh overnight culture of the test strain and was incubated at 37° C. under continuous shaking until an $OD_{600}=0.5$ was reached. Cells were harvested, washed twice with 1×PBS, and adjusted to $1×10^8$ cells/mL. The integrity of the shaved skin of the mice was affected by repeated (seven times) vigorous tape stripping to enable *S. aureus* Newman infection. An inoculum of 15 µL from the bacterial suspension was added to 7-mm filter paper discs, placed onto the prepared skin with two discs per animal, and covered with Finn chambers on Scanpor tape (Smart Practise, Phoenix, Ariz., USA). Finn chamber fixation occurred via Fixomull stretch plasters (BSN medical GmbH, Hamburg, Germany). After incubation for 24 h, the Finn chambers were removed and 1.5 µg of lugdunin per colonised area was applied, followed by a second and third treatment with the same amount of lugdunin after 30 h and 42 h. Six hours after the final application, mice were euthanized, the skin was large-scale detached and 4-mm punches of the originally colonised areas were vortexed in 1×PBS for 30 seconds to remove the attached bacteria from the skin (wash fraction). The skin was dissected with a scalpel to expose bacteria from deeper areas of the skin (tissue fraction), which was homogenized by vortexing in 1×PBS for 30 seconds. CFUs of both fractions were determined by serial dilutions in 1×PBS, which were then spotted onto TSA, supplemented with streptomycin, for *S. aureus* Newman$^{strep}$ specific selection. The plates were incubated overnight at 37° C.

14. Generation of *S. lugdunensis* ΔlugD and Complementation

For the construction of a marker-less knock-out strain, 1-kb flanking regions of lugD were amplified by PCR with the primer pairs lugD upstream-SacI/lugD upstream-Acc65I and lugD downstream-Acc65I/lugD downstream-BglII. The fragments were digested according to their introduced restriction sites and were ligated into the plasmid pBASE6 generating pBASE6-ΔlugD, which was transferred into *E. coli* DC10B. The correct plasmid was transferred to *S. aureus* PS187 by electroporation, which was then infected with the bacteriophage Φ187 for the transduction of pBASE6-ΔlugD into the *S. lugdunensis* IVK28 wild type. The knockout was generated by homologous recombination of the flanking regions into the genome, and deletion of lugD was confirmed by PCR. For the complementation of the mutant, lugD was amplified by the primer pair lugD comp. forw-PstI/lugD comp. rev-Acc65I, digested with the appropriate restriction enzymes and ligated into identically digested pRB474. The constructed pRB474-lugD was transduced into *S. lugdunensis* IVK28 ΔlugD, as described for the knock-out mutant.

15. Competition Assay

*S. lugdunensis* IVK28 wild type, *S. lugdunensis* IVK28 ΔlugD, *S. lugdunensis* IVK28 ΔlugD::pRB474-lugD, and a streptomycin-resistant *S. aureus* Newman were grown in BM overnight at 37° C. under continuous shaking. These strains were then adjusted to $1×10^9$ cells/mL in 1×PBS and diluted 1:10. For the starting condition of 90% *S. aureus*, equal volumes of $1×10^9$ *S. aureus* cells/mL and $1×10^8$ *S. lugdunensis* cells/mL were mixed. Co-cultures with only 10% *S. aureus* were also performed, and 20 µL of these mixtures were spotted in triplicate on BM agar and incubated at 37° C. Samples were taken at 0 h, 24 h, 48 h and 72 h by scraping cells from the agar plates and suspending them in 1×PBS. Serial dilutions of these samples were plated on BM and BM containing streptomycin for selection of S. aureus. After overnight incubation at 37° C., colony counts were determined, and the bacterial ratios of S. aureus and S. lugdunensis were calculated.

16. Co-Colonisation of Cotton Rat Noses

For the colonisation of cotton rat noses, spontaneous streptomycin-resistant mutants of S. lugdunensis IVK28 wild type and S. lugdunensis IVK28 ΔlugD were selected on BM agar plates containing 250 µg/mL streptomycin. Co-colonisation was conducted with S. aureus Newman$^{strep}$. The cotton rat model was described earlier. Since the capacity of S. lugdunensis to colonize cotton rat nares has not been studied before, the inventors determined the inoculum required for stable colonization by IVK28 wild type and its mutant ΔlugD over 5 days. The inventors' previous studies have shown that for S. aureus an inoculum of $10^7$ bacteria per nose results in a constant colonization of about $10^3$ CFUs per nose. To achieve a comparable colonization level with S. lugdunensis, an inoculum of $10^8$ bacteria per nose was required, and there was no detectable difference in colonization efficiency between wild type and ΔlugD. Therefore, co-colonization experiments in cotton rat noses were performed with 10-fold more S. lugdunensis than S. aureus to obtain a 1:1 colonization ratio.

Cotton rats were anesthetized and instilled intranasally with mixtures of either 1×$10^8$ S. lugdunensis wild type/1× $10^7$ S. aureus Newman or 1×$10^8$ S. lugdunensis ΔlugD/1× $10^7$ S. aureus Newman. Five days after bacterial instillation, the animals were euthanized, and noses were surgically removed. The noses were heavily vortexed in 1 mL of 1×PBS for 30 s. Dilutions of the samples in PBS were plated on SSL agar containing 250 µg/mL streptomycin to select for the used strains and to separate S. aureus (yellow) and S. lugdunensis (purple) by colour. The plates were incubated for two days under anaerobic conditions (anaerobic jar with Anaerocult® A, MerckKGaA), for the specific detection of ornithine decarboxylase activity. S. aureus Newman CFUs were determined afterwards. All animals received drinking water with 2.5 mg/mL streptomycin continuously, starting three days prior to the experiment, to reduce the natural nasal flora.

17. Human Colonisation Study

A total of 187 nasal swab samples from hospitalized patients were received from the diagnostics laboratory of the Institute of Medical Microbiology and Hygiene (University Clinic Tuebingen, Germany). Dilutions from each sample were plated on blood agar and SSL agar for a phenotypic identification of S. aureus and S. lugdunensis. Identity was confirmed by coagulase test and matrix-assisted laser desorption/ionization-time-of-flight mass spectrometry (Mass spectrometer: AXIMA Assurance, Shimadzu Europa GmbH, Duisburg, Database: SARAMIS™ with 23.980 spectra and 3.380 super-spectra, BioMérieux, Nuertingen).

B. Results

1. *Staphylococcus lugdunensis* Produces a Highly Potent Antimicrobial Cyclic NRPS-Peptide with Strong Activity Against *Staphylococcus aureus*

In natural habitats, especially in nutrient-poor ecological niches like the human nose [Krismer et al. (2014) Nutrient limitation governs Staphylococcus aureus metabolism and niche adaptation in the human nose. PLoS Pathog 10: e1003862], a fierce competition about available nutrients between colonizing bacteria is assumed. The inventors screened bacterial isolates from nasal swabs for the production of compounds active against S. aureus. Beside activities against a huge range of various nasal bacteria the inventors identified two strains with inhibiting properties against S. aureus. Whereas one isolate, which was identified as *Staphylococcus epidermidis*, exhibited constant production of the antibacterial activity under the investigated conditions, the second isolate, *Staphylococcus lugdunensis* IVK28 was found to have a particularly strong capacity to prevent the growth of S. aureus (FIG. 1). IVK28 showed its antibacterial effect only under iron-limiting conditions. No such inhibitory activity has been described yet for staphylococci. For this reason, this IVK28 designated isolate of S. lugdunensis was further investigated by the inventors.

2. The Genetic Organization of the S. lugdunensis IVK28 NRPS-Operon

Subsequent transposon mutagenesis of the strain resulted in the production-negative mutant M1. Analysis of the insertion site by inverse PCR resulted in the identification of a gene encoding a non-ribosomal peptide synthetase (NRPS; position 860375/76 in the annotated genome sequence of S. lugdunensis N920143; Acc.no: FR870271.1) which is part of the NRPS-II designated system. This clearly indicated that a small peptide might exhibit the antibacterial activity of S. lugdunensis against S. aureus. In the S. lugdunensis genome three putative NRPS-systems have been identified [The entire genome sequence of *Staphylococcus lugdunensis* N920143 is published in Heilbronner, et al. (2011) Genome sequence of *Staphylococcus lugdunensis* N920143 allows identification of putative colonization and virulence factors. FEMS Microbiol Lett 322: 60-67, which is incorporated herein by reference]. Whereas NRPS-I exhibits high homologies to the S. aureus NRPS dipeptide system encoding aureusimine A and B [Wyatt et al. (2010) *Staphylococcus aureus* nonribosomal peptide secondary metabolites regulate virulence. Science 329: 294-296] [Erratum in Science, 2011 Sep. 9; 333 (6048):1381], and NRPS-III has striking similarities to described siderophore systems (Heilbronner et al., cit loc.) nothing is known about the potential product encoded by NRPS-II. Investigation of the published genomes of S. lugdunensis (completed sequences of strains N920143, HKU09-01 and partial sequences of strains VCU139 and M235909 (can easily determined on the basis of the genome sequence of *Staphylococcus lugdunensis* N920143. HKU09-01: between 864800/864801) showed that the applying NRPS-II operon is present in every strain sequenced so far and therefore does not depict a strain specific feature. Nevertheless, the published genomes do contain various potential sequencing errors or real frameshift mutations, leading to different annotations. For this reason, all relevant positions, indicating a potential frameshift, were amplified by PCR from strain IVK28. Subsequent sequencing of the PCR products revealed that the sequence of IVK28 corresponds to that of strain N920143 and its annotation, except for the annotated nucleotide position 863515 which is located at the 3'-end of gene SLUG_08110. In contrast to N920143, in IVK28 there is a stretch of eight instead of seven adenosine-nucleotides, leading to the fusion of genes SLUG_08110 and SLUG_08120 to one open reading frame.

Figure 2:
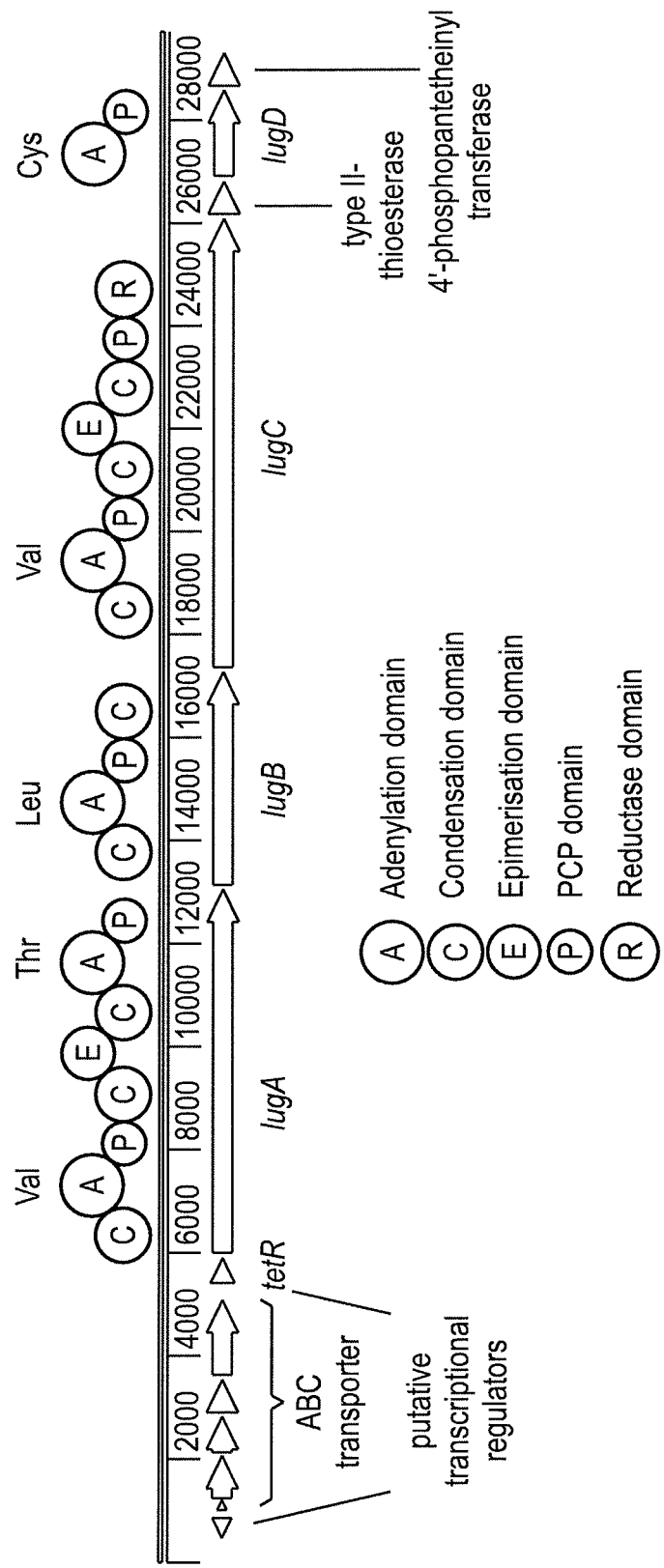
FIG. 2 shows the genetic locus required for the synthesis of lugdunin and the domain architecture of the *S. lugdunensis* IVK28 non-ribosomal peptide synthetases with predicted specificities.

FIG. 2 depicts the genetic organization of the 29.6 kb NRPS-II operon in S. lugdunensis IVK28. The locations of the coding sequences are indicated in the following sequence information of the S. lugdunensis IVK28 NRPS-operon:

LOCUS    nrp-operon IVK28    29605 bp    DNA    linear
FEATURES    Location/Qualifiers

| | |
|---|---|
| misc_feature | complement (427..936)<br>/note="transcriptional regulator of GntR family." |
| misc_feature | 1253..2143<br>/note="ABC transporter (GdmF type multidrug transport system)" |
| misc_feature | 2140..2904<br>/note="ABC-2 type transport system permease protein" |
| misc_feature | 2917..3630<br>/note="ABC transporter" |
| misc_feature | 3623..5164<br>/note="hyp. membrane protein" |
| misc_feature | 5409..5981<br>/note="TetR/AcrR family regulator" |
| misc_feature | 6007..13131<br>/note="lugA" (corresponds to SLUG_08100 of Staphylococcus lugdunensis N920143) |
| misc_feature | 13121..17341<br>/note="lugB" corresponds to the fused sequence of SLUG_08110 and SLUG_08120 (by insertion of one additional nucleotide) of Staphylococcus lugdunensis N920143) |
| misc_feature | 17359..26172<br>/note="lugC" corresponds to SLUG_08130 of Staphylococcus lugdunensis N920143) |
| misc_feature | 26169..26855<br>/note="Thioesterase family protein" |
| misc_feature | 26893..28632<br>/note="lugD" corresponds to SLUG_08150 of Staphylococcus lugdunensis N920143) |
| misc_feature | 28640..29293<br>/note="4'-phosphopantetheinyltransferase" |
| misc_feature | 1027..1266<br>/note="put. negative regulator of sigY (in Bacillus" |
| misc_feature | 10338..10347<br>/note="Tn917 insertion site" |
| BASE COUNT | 11616 a   3273 c   4650 g   10066 t |

Interestingly, with only 26.7% the GC-content of the NRPS-operon is significantly lower than the overall GC-content of the genome (33.8%), indicating horizontal gene transfer from an extremely low GC-organism. The operon contains four consecutive genes (named lugA, B, C, D) encoding NRPS proteins, interrupted by a type II thioesterase gene between lugC and lugD. In the 5'-region two ABC-transporters and two potential regulatory genes are encoded. At the 3'-end of the operon the 4'-phosphopantetheinyl-transferase is encoded. Although the antimicrobial activity could only be detected under iron-limited conditions, no obvious fur-box could be identified within the operon, indicating a rather indirect effect of lack of iron on the expression of the operon.

This so-called lug operon was exclusively found in *S. lugdunensis* and encodes a unique combination of antibiotic biosynthesis enzymes, all with less than 35% identity to any other described enzyme, suggesting that it may be responsible for biosynthesis of a novel compound. To confirm that the lug operon is responsible for the antimicrobial activity of IVK28, the smallest NRPS gene, lugD, was deleted by gene replacement. The mutant ΔlugD showed no detectable antimicrobial activity, but the phenotype was restored by complementation with a plasmid-encoded copy of lugD (FIG. 1).

Computational analysis (NRPS predictor 2, Anti-Smash, HMMER) of the proteins encoded by lugA-D revealed an uncommon domain architecture, which is shown in FIG. 2. Most NRPS-systems assemble activated amino acids in a linear fashion until product release, which is usually catalyzed by a type I thioesterase. In contrast, the *S. lugdunensis* operon exhibits a putative reductase domain for final product release, encoded at the end of the lugC. At the same time, differing from LugA-C, LugD lacks a condensation domain, which is a common feature for so called initiation modules that provide the first amino acids in some NRPS systems. The subsequent condensation reaction is then catalyzed by one of the elongation modules.

Adenylation-domain specificity prediction with the NRPS predictor 2 and Anti-Smash software gave valine and threonine (LugA), leucine (LugB), valine (LugC) and cysteine (LugD) as the most likely activated amino acids, although with different probabilities (60% for Thr and 100% for Cys).

3. Identification of the NRPS-II Product

Figure 3A:
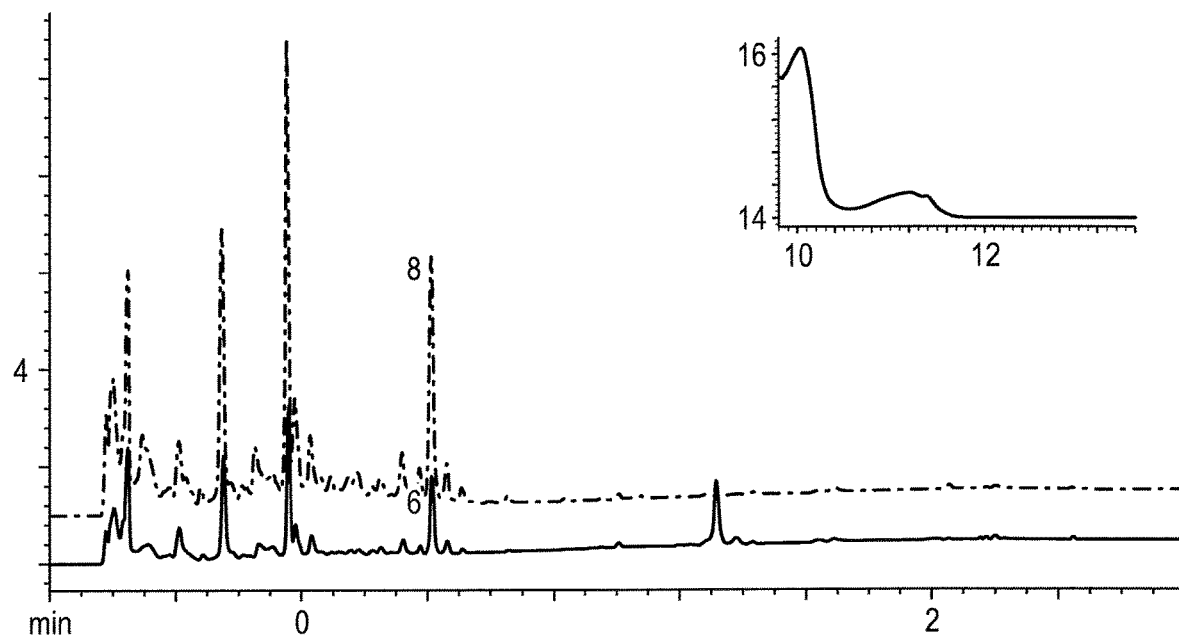
FIGS. 3A and 3B show the identification of the NRPS-II product in cell extracts of *S. lugdunensis* IVK28.
Figure 3B:
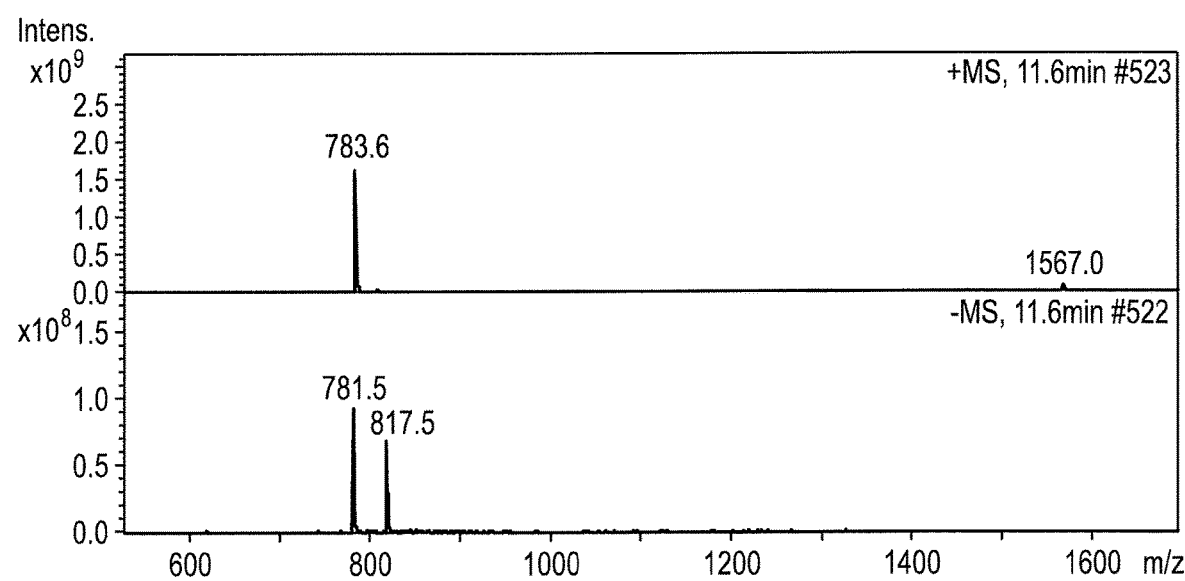

Since the inhibitory activity against *S. aureus* only was detectable on agar plates containing 200 μM 2,2'-bipyridine, the same conditions were used for an extraction attempt of the peptide. After growth for 48 hours cells of *S. lugdunensis* IVK28 were scraped off the agar and extracted with 100% ethanol. Subsequent HPLC analysis of extracts from the wild-type and the M1 mutant strain revealed differences in only one main peak at 10.6 min retention time (with a molecular mass of 782.5 Da (FIGS. 3 A and B). Surprisingly, the absorbance spectrum showed characteristics of tryptophan containing proteins at 280 nm, although no such amino acid has been predicted according to the genetic organization in silico. To confirm that the absence of the respective HPLC-peak is in fact due to the integration of the transposon in lugA and not because of an unidentified second-site mutation, a defined knock-out strain of lugD was constructed (ΔlugD::erm). As expected, the HPLC chromatogram of the respective ΔlugD -mutant was nearly identical to the one of *S. lugdunensis* M1 and did not show the peak at 10.6 min (data not shown). The production phenotype could partially be restored by complementation with the plasmid pRB474-lugD.

Figure 4A:
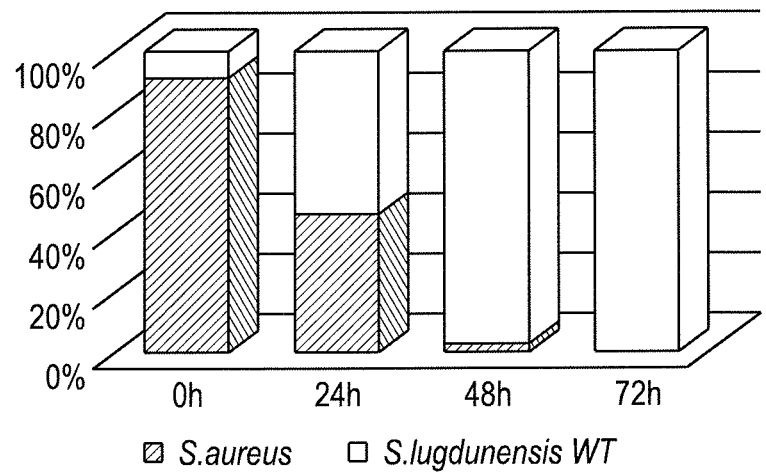
FIGS. 4A to 4C show that *S. lugdunensis* IVK28 is able to eliminate *S. aureus* USA300. *S. aureus* USA300 (black) and *S. lugdunensis* IVK28 wild type (FIG. 4A) or mutant ΔlugD (FIG. 4B and FIG. 4C) (white) were mixed in varying ratios (10:1 (FIG. 4A and FIG. 4B) or 1:10 (FIG. 4C)) and spotted on BM-agar containing 2,2'-bipyridine. After the indicated time points the ratio of the strains in the spot was determined. The figures represent the mean of three experiments.
Figure 4B:
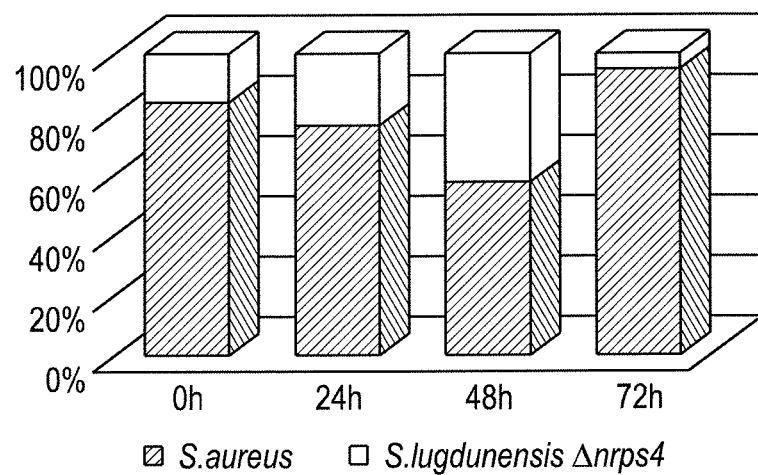
Figure 4C:
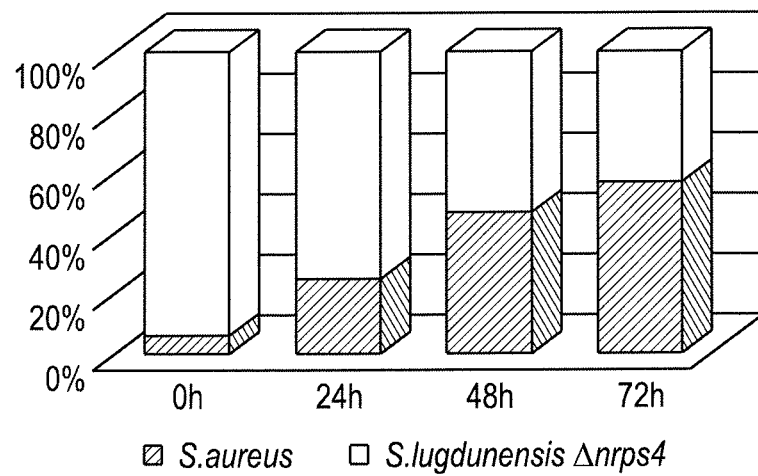

4. *S. lugdunensis* IVK28 is Able to Eliminate *S. aureus* USA300 in Co-Cultivation Experiments To investigate if the expression of the NRPS-II system gives *S. lugdunensis* a competitive advantage, strains IVK28 or ΔlugD::erm were co-cultivated in varying ratios with *S. aureus* USA300 on 2,2'-bipyridine containing agar plates. As shown in FIG. 4, *S. lugdunensis* IVK28 was able to completely eradicate *S. aureus* USA300 from the mixture within 72 hours, even with 90% *S. aureus* at the starting conditions (A). In contrast, the mutant *S. lugdunensis* ΔlugD::erm only slightly decreased the *S. aureus* ratio within the first 48 hours and was subsequently overgrown by *S. aureus* within 72 hours (B). Even more, *S. aureus* was able to displace the mutant when the starting conditions contained 90% *S. lugdunensis* (C). These results clearly demonstrate the importance of the NRPS-II system as a fitness-factor of *S. lugdunensis* in the struggle against *S. aureus*. Of note, the results were nearly identical when 2,2'-bipyridine was omitted from the medium, indicating that iron-limitation might not be the true and only inducing signal, but rather a special kind of stress like the close contact with *S. aureus*.

5. Overproduction and Purification of the NRPS-II Peptide

Figure 5A:
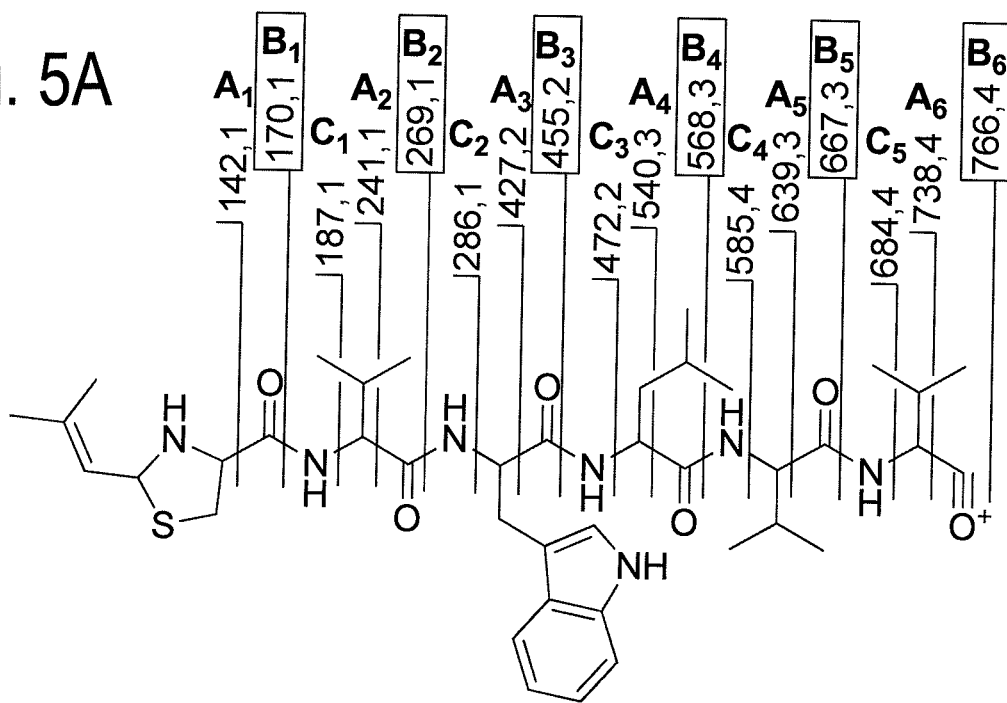
FIG. 5A shows the HPLC-MS-MS fragments and FIG. 5B shows the structural formula of the cyclic peptide embodying the compound according to the invention ("lugdunin")
Figure 5B:
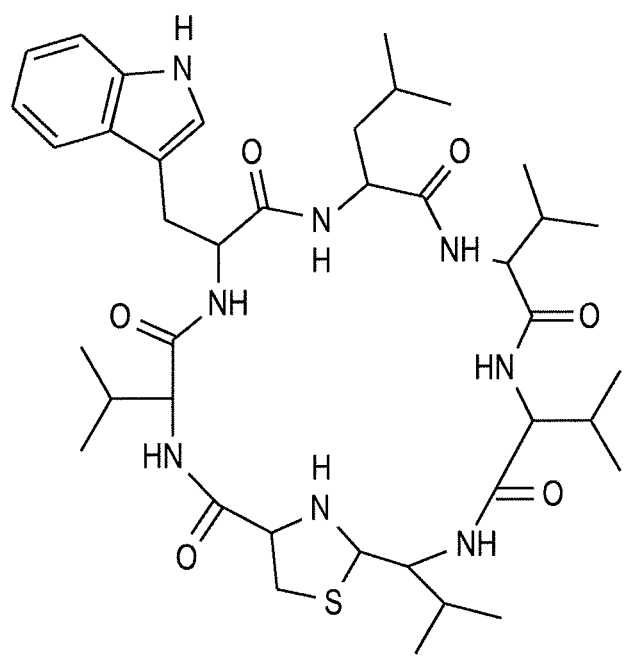

Interestingly, no antimicrobial activity could be detected, when *S. lugdunensis* IVK28 was grown in 2,2'-bipyridine containing liquid cultures, neither in cell extracts nor in the culture supernatant. For this reason the strain was genetically engineered by replacing the tetR-family like repressor gene upstream of lugA with the well-established xylose-inducible xylR-regulatory system. This enabled the inventors to induce peptide production by the addition of 0.5% xylose and in the absence of bipyridine. The corresponding strain ΔtetR::erm/xylR exhibited significant antimicrobial activity in the culture supernatant after xylose addition. By 1-butanol extraction the inventors were able to concentrate the antimicrobial activity in the solvent. After evaporation of 1-butanol, resuspension in 100% methanol and size exclusion chromatography on a Sephadex LH-20 column a highly enriched active fraction could be obtained. Final purification was performed by preparative HPLC, resulting in the pure antimicrobial compound, which was solved and stored in DMSO at a concentration of 10 mg/ml at −20° C. LC-MS and MS-MS analysis confirmed the before ascertained molecular weight of 782.5 Da with the elemental formula $C_{40}H_{62}N_8O_6S$ (FIG. 5).

An embodiment of the compound according to the invention named "lugdunin" was isolated as a white solid, the UV spectrum pointed to an indole ring and HR-ESI-MS revealed an ion peak at m/z=783.4581 ([M+H]$^+$) and specific fragments in HPLC-MS-MS. Marfey's modification products of D- and L-amino acid standards and of lugdunin were also subjected to HPLC-ESI-MS and HPLC-MS-MS. Mass adducts and fragments revealed D- and L-amino acids corresponding to three valine, leucine/isoleucine, tryptophan and a novel fragment for $C_8H_{15}N_2OS$ assigned to a thiazolidine ring structure. The $^1$H-NMR spectrum showed characteristic aliphatic signals for the valine protons and characteristic signals for the tryptophan moiety. The NMR spectra pointed to at least two different isomers and conformers for lugdunin due to altered chemical shifts after 48 hours in solution. Additional 2D NMR experiments supported the structure of lugdunin. However, overlapping signals did not allow for the full determination of the regiochemistry by NMR methods nor the stereochemistry of the single amino acids of lugdunin, the order of the D- and L-valine residues is not assignable via NMR spectroscopy. Therefore, lugdunin is assigned to the cyclic peptide depicted in FIGS. 5A and B generated from the 7 amino acids and the empirical formula $C_{40}H_{62}N_8O_6S$.

6. The New Compound is Bactericidal and Mainly Active Against Major Human Pathogens To determine the spectrum of activity, a range of clinically relevant Gram-positive and Gram-negative bacteria were used for MIC-determination. As shown in Table 1, it could be confirmed that beside various *S. aureus* strains the new compound is active against all tested species, including the glycopeptide-intermediate resistant *S. aureus* (GISA) and vancomycin resistant (VRE) *Enterococcus faecalis* and *E. faecium*, *Streptococcus pneumoniae* and *Listeria monocytogenes*. MICs ranging from 1.5 to 12 µg/ml (1.9 to 15 µM) underscore the strong antibacterial potential of lugdunin. Interestingly, the *S. aureus* USA300 MRSA strain was more susceptible than the laboratory strain RN4220. The producer strain showed also activity against *Propionibacterium acnes*, *Streptococcus pyogenes*, *Micrococcus luteus* and a range of other staphylococci. None of the Gram-negative bacteria was significantly inhibited in the investigated concentration range (up to 100 µg/ml).

TABLE 1

MIC determination of lugdunin against various bacteria; MRSA, methicillin-resistant *S. aureus*; GISA, glycopeptide-resistant *S. aureus*; VRE, vancomycin-resistant enterococci

| STRAIN | MIC | Resistance |
|---|---|---|
| *Staphylococcus aureus* USA 300 (LAC) | 1.5 µg/ml | MRSA |
| *Staphylococcus aureus* USA300 (NRS384) | 1.5 µg/ml | MRSA |
| *Staphylococcus aureus* Mu50 | 3 µg/ml | GISA |
| *Staphylococcus aureus* SA113 | 3 µg/ml | |
| *Staphylococcus aureus* RN4220 | 3 µg/ml | |
| *Enterococcus faecalis* VRE366 | 12 µg/ml | VRE |
| *Enterococcus faecium* BK463 | 3 µg/ml | VRE |
| *Listeria monocytogenes* ATCC 19118 | 6 µg/ml | |
| *Streptococcus pneumoniae* ATCC 49619 | 1.5 µg/ml | |
| *Pseudomonas aeruginosa* PAO1 | >50 | |
| *Escherichia coli* DH5α | >50 | |

Figure 6A:
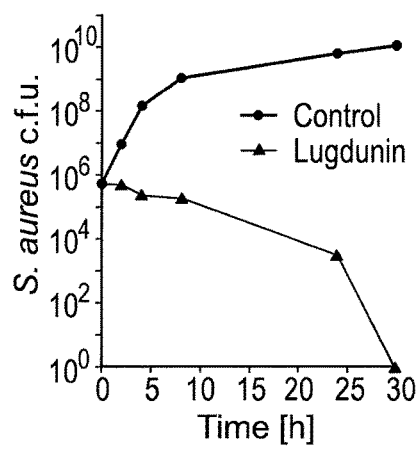
FIGS. 6A and 6B show that lugdunin has bactericidal activity and no tendency to induce spontaneous resistance.
Figure 6B:
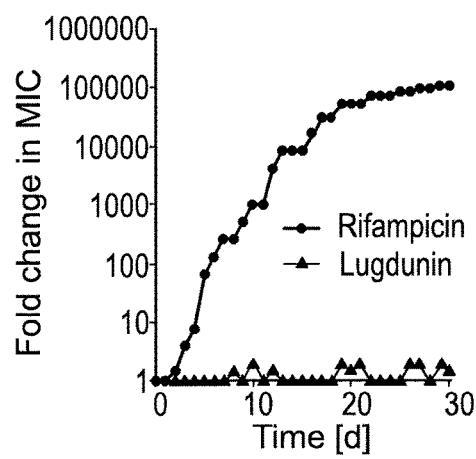

Lugdunin was bactericidal against MRSA with complete killing after a single dose treatment (FIG. 6A). No spontaneous resistance development was observed in *S. aureus* during continuous subcultivation of *S. aureus* with subinhibitory concentrations of lugdunin over 30 days (FIG. 6B). In contrast, treatment with rifampicin led to rapidly increasing spontaneous resistance within a few days (FIG. 6B).

Figure 7:
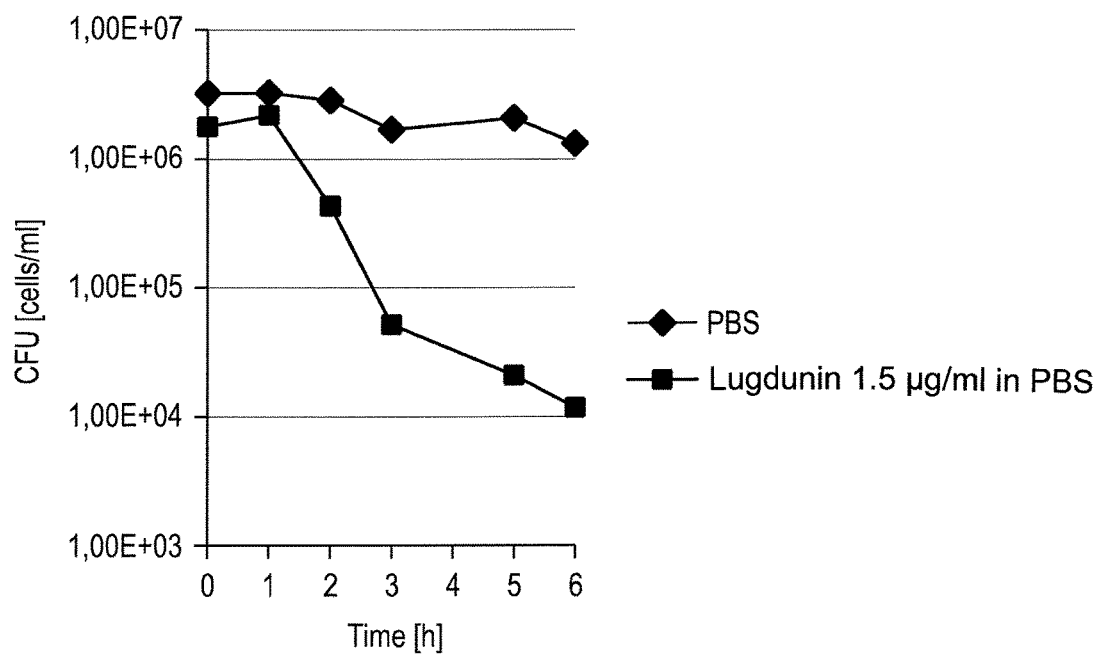
FIG. 7: shows that lugdunin exhibits bactericidal activity against non-growing *S. aureus* USA300. Incubation of *S. aureus* USA300 with 1.5 µg/ml lugdunin leads to an at least 100-fold decrease of viable cells in PBS within 6 hours.

To test whether the activity is bacteriostatic or bactericidal, killing assays were performed with *S. aureus* USA300 and peptide concentrations of 1×MIC (1.5 µg/ml). As shown in FIG. 7, a reduction of viable cells of at least two log units was achieved within 6 hours incubation in PBS, clearly indicating a bactericidal mode of action.

7. Topical Treatment with Lugdunin is Effective in an In Vivo Mouse Model

Since the effectiveness of lugdunin could be shown in vitro, the next step was the development of an in vivo model. For this purpose the so called tape stripping model was applied [Wanke et al. (2013) *Staphylococcus aureus* skin colonization is promoted by barrier disruption and leads to local inflammation. Exp Dermatol 22: 153-15]. For this model the back of C57BL/6 mice was shaved and the skin barrier was disrupted by strong tape-stripping (7 times) without creating wounds. *S. aureus* Newman (inoculum of $10^7$ cfu in 15 µl phosphate buffered saline (PBS)) was applied on the disrupted skin and covered by Finn Chambers for 20 hours to ensure efficient colonization. Due to its hydrophobic nature lugdunin was solved in 100% DMSO to a concentration of 10 mg/ml and subsequently diluted into 100% sesame oil to a final concentration of 100 µg/ml. 15 µl of this lugdunin preparation were applied to the colonized spots 18, 24, and 42 hours after the application of S. aureus. For the control only 1% DMSO in sesame oil was applied. Three hours after the final application mice were sacrificed and skin biopsy punches were analyzed for the presence of S. aureus. The inventors distinguished between the washing fraction (loosely attached bacteria removed by a washing step in PBS) and the scrape fraction (destruction of the skin material with scalpels to release bacteria from deep skin areas). FIG. 8 clearly shows the reduction of S. aureus by lugdunin treatment after 45 hours in the wash fraction as well as in the scrape fraction, indicating that lugdunin is also penetrating deeper tissue areas.

Figure 9:
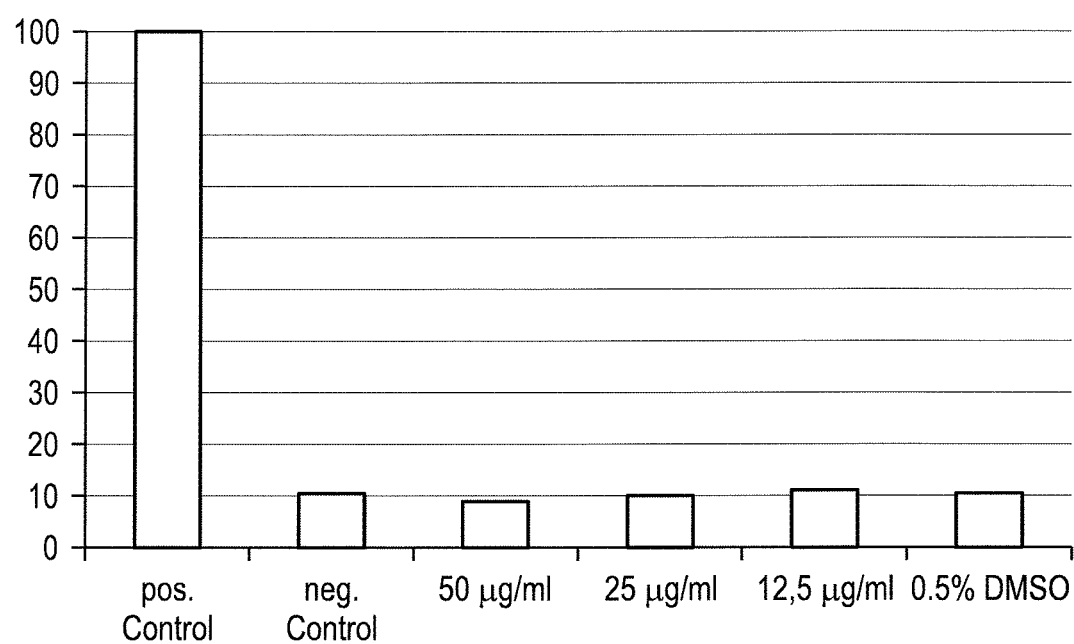
FIG. 9: shows a cytotoxicity test or the determination of potential cytotoxic effects on neutrophil granulocytes within 3 h incubation.

In a preliminary experiment, where the lactate-dehydrogenase release of neutrophil granulocytes was measured, no significant cytotoxicity could be observed within 3 h incubation of the cells with the peptide, even at concentrations of 50 µg/ml resembling a more than 30-fold MIC for S. aureus USA300; see FIG. 9.

8. Lugdunin Production Outcompetes S. aureus

The production of antimicrobials, mostly plasmid-encoded ribosomally synthesized bacteriocins, has been sporadically documented in individual bacterial strains from human microbiomes. However, the roles of such compounds in microbial fitness and in microbiota dynamics have remained largely unknown. To determine whether lugdunin contributes to the capacity of S. lugdunensis IVK28 to prevail in competition with S. aureus, the two species were co-cultivated on solid agar surface, promoting lugdunin production, and bacterial numbers were monitored for three days.

As shown in FIG. 10A, the lugdunin-producing IVK28 wild type overgrew S. aureus efficiently, even when the inoculum contained 10-times higher numbers of S. aureus than S. lugdunensis cells. No viable S. aureus cells were recovered after three days indicating complete killing by S. lugdunensis. In contrast, IVK28 ΔlugD was overgrown by S. aureus even when it was inoculated at 10-times higher numbers than S. aureus (FIGS. 10 B, D). The S. aureus-eradicating capacity of ΔlugD could be largely restored by complementation with lugD on a plasmid (FIG. 10 C). These data demonstrated that S. lugdunensis can effectively eradicate S. aureus and that lugdunin production is responsible for this trait.

Figure 11A:
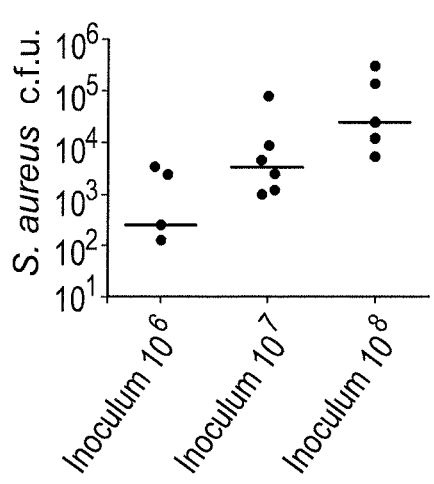
FIGS. 11A to 11C show the nasal colonization rates in cotton rats of *S. aureus* and *S. lugdunensis*. Different inocula of *S. aureus* Newman (FIG. 11A), *S. lugdunensis* IVK 28 wild type (FIG. 11 B) and *S. lugdunensis* IVK 28 ΔlugD (FIG. 11C) were instilled intranasally to determine their colonization efficiency in cotton rats. CFUs of each strain were determined per nose after 5 days and plotted as individual dots in FIGS. 11A-11C. Lines represent the median of each group.
Figure 11B:
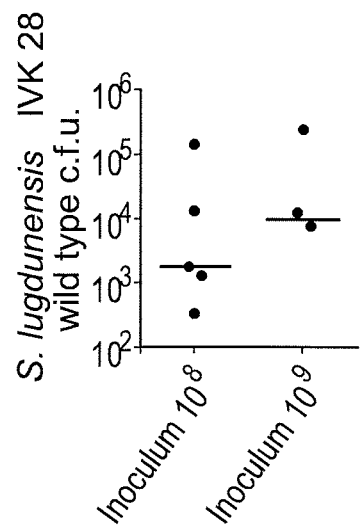
Figure 11C:
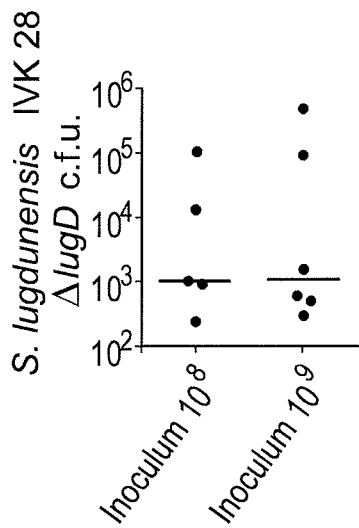

Nasal carriage is known to be a major risk factor for invasive S. aureus infections. To explore whether S. lugdunensis can interfere with nasal S. aureus colonisation in vivo in vertebrates, the noses of cotton rats, a well-established animal model for investigating S. aureus nasal colonisation, were instilled with mixtures of S. lugdunensis IVK28 wild type or ΔlugD plus S. aureus. The three test strains colonised cotton rat noses stably over the 5-day test period when instilled individually (FIG. 11). However, when the two species were co-inoculated, significantly less S. aureus cells were retrieved from animals co-colonised by IVK28 wild type compared to those co-colonised with ΔlugD (FIG. 10 E). This finding indicates that lugdunin production can effectively interfere with S. aureus colonisation in vivo.

Figure 12:
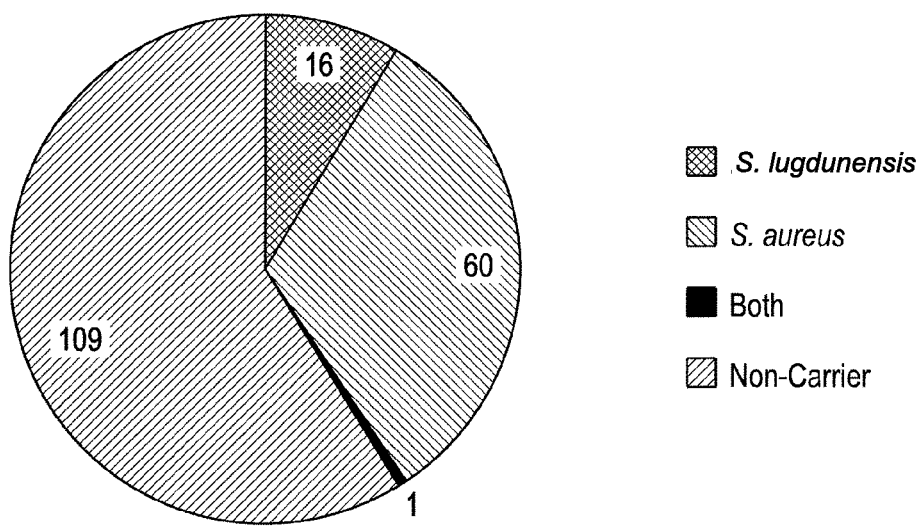
FIG. 12: shows the distribution of carriage of *S. aureus, S. lugdunensis*, and both in a sample of 187 risk patients.

9. The Presence of S. lugdunensis in the Human Nose is Very Likely Correlated with the Absence of S. aureus As a proof of principle of the influence of S. lugdunensis on S. aureus we investigated the co-occurrence of the two species in human noses. For this, nasal swabs of 187 risk patients were investigated. In total 61 individuals were colonized with S. aureus (32.6%) and 17 with S. lugdunensis (9.1%). None of the species was found in 109 people (58.2%). From these numbers 2.97% (nearly 6 individuals) can be expected to be co-colonized with S. aureus and S. lugdunensis. In contrast, only one person was identified being co-colonized, which is significantly less than expected (FIG. 12, $p<0.05$). This might indicate that in vivo the presence of S. lugdunensis inhibits the colonization with S. aureus by the secretion of lugdunin. In line with this assumption is the detection of the mass of lugdunin (782.4513 Da) in butanol extracted swabs of S. lugdunensis carriers, but not of non-carriers (data not shown).

10. Biological Activity of Lugdunin Derivatives

The inventors have synthesized numerous chemical derivatives of lugdunin to evaluate an abstract or general chemical formula representing the prototype of the newly found anti-bacterial activity. The chemical derivatives are shown in the subsequent tables. All synthetic derivatives were tested for biological activity against S. aureus USA300. Measured values resulting therefrom were classified and marked with "+". Derivatives marked with "+" result in the respective concentration range a complete inhibition of the bacterial growth, i.e. no growth. The categories are evident from the following Table 2.

TABLE 2

| MIC in pg/ml | | | | | |
|---|---|---|---|---|---|
| 200 | 100 | 50 | 25 | 12.5 | 1.5 |
| − | + | ++ | +++ | ++++ | |
| inactive | slightly active | active | | very active | |

Thus, the indication of a biological activity with "++++" means a MIC between 1.5 and 12.5 µg/ml. Lugdunin is the references substance with the highest biological activity and a MIC of 1.5 µg/ml. In addition to derivatives resulting in a complete killing of the USA300 test strain derivatives were synthesized which induce a significant growth reduction. They do not result in a complete killing of all bacterial cells of the test strain. Such derivatives are marked with "♦".

TABLE 3

Formula (I)

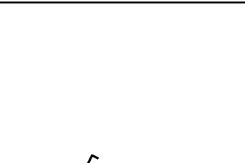

Special case for the derivative with L-Ala at position 1 (derivative 6 from Tab. 3). Here no closing of the thiozolidine ring occurs. The resulting imine (left) or the half aminale (right) however show biological activity.

Variable cycle sizes and hetero atoms in the thiazolidin cycle.
m = 1 and 2; n = 0, 1; Y = S, O, $CH_3$ (special case upper right box)

| | | | | | | | |
|---|---|---|---|---|---|---|---|
| 1-L-Cys | 2-D-Val | 3-L-Trp | 4-D-Leu | 5-L-Val | 6-D-Val | 7-D-Val | ⇐ Sequence of the natural substance Bioactivity against *S aureus* USA 300 X #1 ↓ |
| | | | | For "m" ↓ | | | |
| 1-L-Homoserine | 2-D-Val | 3-L-Trp | 4-D-Leu | 5-L-Val | 6-D-Val | 7-L-Val | ♦ |
| | | | | For "n" ↓ | | | |
| 1-L-Cys | ■ | 3-L-Trp | 4-D-Leu | 5-L-Val | 6-D-Val | 7-L-Val | ♦ |
| 1-L-Cys | ■ | 3-L-Trp | 4-D-Leu | 5-L-Leu | 6-D-Leu | 7-L-Val | + |
| | | | | For "Y" ↓ | | | |
| 1-L-Cys | 2-D-Val | 3-L-Trp | 4-D-Leu | 5-L-Val | 6-D-Val | 7-L-Val | ++++ |
| 1-L-Ser | 2-D-Val | 3-L-Trp | 4-D-Leu | 5-L-Val | 6-D-Val | 7-L-Val | ++ |
| | | | | Special case ↓ | | | |
| 1-L-Ala | 2-D-Val | 3-L-Trp | 4-D-Leu | 5-L-Val | 6-D-Val | 7-L-Val | ♦ |

TABLE 4

Formula (II)

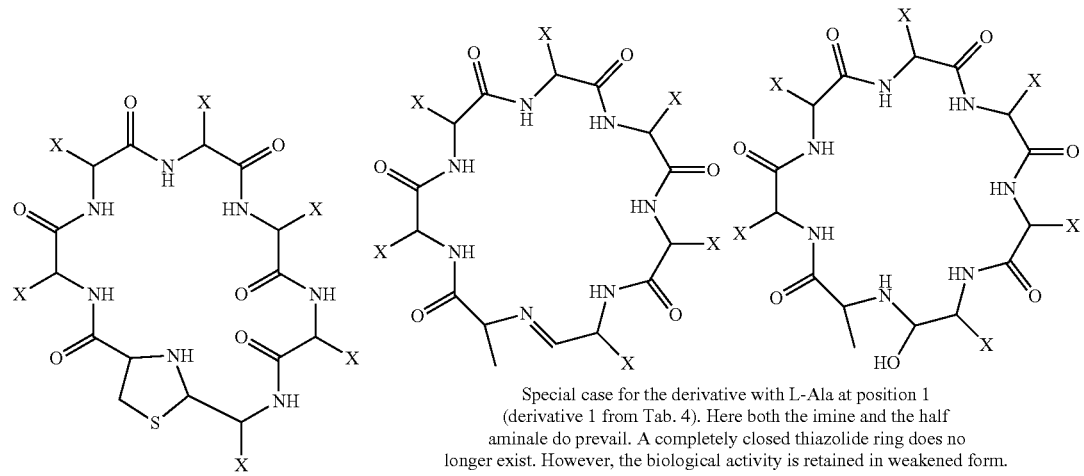

Special case for the derivative with L-Ala at position 1
(derivative 1 from Tab. 4). Here both the imine and the half
aminale do prevail. A completely closed thiazolide ring does no
longer exist. However, the biological activity is retained in weakened form.

| 1-L-Cys | 2-D-Val | 3-L-Trp | 4-D-Leu | 5-L-Val | 6-D-Val | 7-D-Val | ⇐ Sequence of the natural substance |
|---|---|---|---|---|---|---|---|
| X #1 ↓ | X #2 ↓ | X #3 ↓ | X #4 ↓ | X #5 ↓ | X #6 ↓ | X #7 ↓ | Bioactivity against *S aureus* USA 300 X #1 ↓ |
| 1-L-Ala | 2-D-Val | 3-L-Trp | 4-D-Leu | 5-L-Val | 6-D-Val | 7-L-Val | + |
| 1-L-Cys | 2-D-Ala | 3-L-Trp | 4-D-Leu | 5-L-Val | 6-D-Val | 7-L-Val | +++ |
| 1-L-Cys | 2-D-Leu | 3-L-Trp | 4-D-Leu | 5-L-Val | 6-D-Val | 7-L-Val | ++++ |
| 1-L-Cys | 2-L-Val | 3-L-Trp | 4-D-Leu | 5-L-Val | 6-D-Val | 7-L-Val | ++ |
| 1-L-Cys | 2-D-Val | 3-L-Ala | 4-D-Leu | 5-L-Val | 6-D-Val | 7-L-Val | ◆ |
| 1-L-Cys | 2-D-Val | 3-L-DOPA | 4-D-Leu | 5-L-Val | 6-D-Val | 7-L-Val | ◆ |
| 1-L-Cys | 2-D-Val | 3-L-Tyr | 4-D-Leu | 5-L-Val | 6-D-Val | 7-L-Val | + |
| 1-L-Cys | 2-D-Val | 3-L-Phe | 4-D-Leu | 5-L-Val | 6-D-Val | 7-L-Val | +++ |
| 1-L-Cys | 2-D-Val | 3-L-Trp | 4-D-Ala | 5-L-Val | 6-D-Val | 7-L-Val | ◆ |
| 1-L-Cys | 2-D-Val | 3-L-Trp | 4-D-Leu | 5-L-Ala | 6-D-Val | 7-L-Val | +++ |
| 1-L-Cys | 2-D-Val | 3-L-Trp | 4-D-Leu | 5-L-Thr | 6-D-Val | 7-L-Val | ++ |
| 1-L-Cys | 2-D-Val | 3-L-Trp | 4-D-Leu | 5-L-Val | 6-D-Ala | 7-L-Val | ++ |
| 1-L-Cys | 2-D-Val | 3-L-Trp | 4-D-Leu | 5-L-Val | 6-D-Thr | 7-L-Val | + |
| 1-L-Cys | 2-D-Val | 3-L-Trp | 4-D-Leu | 5-L-Val | 6-D-Trp | 7-L-Val | ++++ |
| 1-L-Cys | 2-D-Val | 3-D-Anthranyl-Ala | 4-D-Leu | 5-L-Val | 6-D-Trp | 7-L-Val | ◆ |
| 1-L-Cys | 2-D-Val | 3-L-Ala | 4-D-Leu | 5-L-Val | 6-D-Trp | 7-L-Val | + |
| 1-L-Cys | 2-D-Val | 3-L-Val | 4-D-Val | 5-L-Leu | 6-D-Trp | 7-L-Val | ++++ |
| 1-L-Cys | 2-L-Val | 3-D-Val | 4-L-Val | 5-D-Leu | 6-L-Trp | 7-L-Val | +++ |
| 1-D-Cys | 2-L-Val | 3-D-Trp | 4-L-Leu | 5-D-Val | 6-L-Val | 7-L-Val | +++ |

TABLE 5

Formula (III)

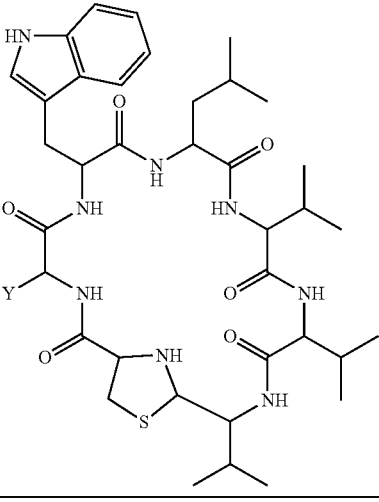

Modification: Free stereochemistry and variable position 2

| | | | | | | |
|---|---|---|---|---|---|---|
| 1-L-Cys | 2-D-Val | 3-L-Trp | 4-D-Leu | 5-L-Val | 6-D-Val | 7-D-Val ⇐ Sequence of the natural substance |
| | Y #2 ↓ | | | | | Bioactivity against *S aureus* USA 300 X #1 ↓ |
| 1-L-Cys | 2-D-Leu | 3-L-Trp | 4-D-Leu | 5-L-Val | 6-D-Val | 7-L-Val ++++ |
| 1-L-Cys | 2-D-Ala | 3-L-Trp | 4-D-Leu | 5-L-Val | 6-D-Val | 7-L-Val +++ |
| 1-L-Cys | 2-L-Val | 3-L-Trp | 4-D-Leu | 5-L-Val | 6-D-Val | 7-L-Val ++ |
| 1-D-Cys | 2-L-Val | 3-D-Trp | 4-L-Leu | 5-D-Val | 6-L-Val | 7-L-Val +++ |
| 1-L-Cys | 2-L-Val | 3-D-Val | 4-L-Val | 5-D-Leu | 6-L-Trp | 7-L-Val +++ |

TABLE 6

Formula (IV)

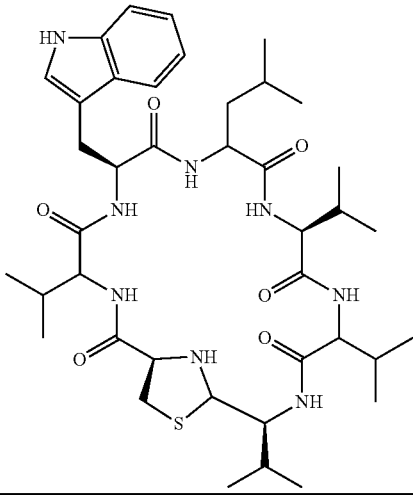

Lugdunin naural substance as it is isolated from *S. Lugdunensis* (MIC = 1.5 μg/ml)

| 1-L-Cys | 2-D-Val | 3-L-Trp | 4-D-Leu | 5-L-Val | 6-D-Val | 7-L-Val | ++++ |
|---|---|---|---|---|---|---|---|

From theses experiments the inventors were able to identify an abstract or general chemical formula representing the prototype of the newly found anti-bacterial activity. Such formula is depicted in claim 1. The substituents m, n, X, and Y can be varied within the indicated ranges without losing the anti-bacterial activity, as it is demonstrated by these experiments.

9. Summary

Here the inventors describe the isolation and structure elucidation of the novel bactericidal peptide antibiotic lugdunin, which is active against *S. aureus* and other pathogenic bacterial species. On the basis of this peptide derivatives have been synthesized and tested for their anti-bacterial activity. As a result, a core structure has been developed by the inventors, which exhibits the observed activity.

The isolated naturally occuring peptide is non-ribosomally produced by a *Staphylococcus lugdunensis* isolate (strain IVK28) where the corresponding NRPS-operon is chromosomally encoded. However, genome database analysis and PCR-amplification experiments with 14 natural isolates indicated that the operon is present in all investigated strains, although not all of them exhibited the antibiotic activity (data not shown). Except for the description of micrococcin P1 production in the single animal associated *Staphylococcus equorum* strain WS2733 (Carnio et al. (2001) Pyridinyl polythiazole class peptide antibiotic micrococcin P1, secreted by foodborne *Staphylococcus equorum* WS2733, is biosynthesized nonribosomally. Eur J Biochem 268: 6390-6401), no NRPS-peptides are known for the genus *Staphylococcus* that exhibit antibacterial properties. Micrococcin P1 was originally identified in *Micrococcus varians* and *Bacillus pumilus*, but lugdunin represents the first genus-specific antibacterial NRPS product with a novel structure for Staphylococci. Since *S. lugdunensis* can be frequently isolated from the human nose, it is a potential competitor of *S. aureus* in this habitat. The inventor's co-cultivation experiments have clearly shown that the production of lugdunin equips *S. lugdunensis* with a strong advantage in competition. Even a minority of *S. lugdunensis* IVK28 cells at the starting conditions can eradicate *S. aureus* from the culture within 72 hours. Also, purified lugdunin is effective in eradication of *S. aureus* in a mouse model (tape stripping model).

Lugdunin represents a novel and rather uncommon structure since it comprises a tryptophan residue in combination with three consecutive valine residues, of which one is part of a valinoyl-thiazolidine ring structure. Tryptophan and the thiazolidine portion are flanking a fourth valine residue. A high content of alternating D- and L-valine has been found in the macrolactone antibiotic valinomycin, which acts as an ionophor, but there is no structural similarity to lugdunin. A combined L-tryptophan-thiazole structure has been described for the protein synthesis inhibitors A21459 [Ferrari et al. (1996) Antibiotics A21459 A and B, new inhibitors of bacterial protein synthesis. II. Structure elucidation. J Antibiot (Tokyo) 49: 150-154], Kocurin [Martin et al. (2013) Kocurin, the true structure of PM181104, an antimethicillin-resistant *Staphylococcus aureus* (MRSA) thiazolyl peptide from the marine-derived bacterium *Kocuria palustris*. Mar Drugs 11: 387-398], or the 7-methoxy-tryptophan containing zelkovamycin [Tabata N, Tomoda H, Zhang H, Uchida R, Omura S (1999) Zelkovamycin, a new cyclic peptide antibiotic from *Streptomyces* sp. K96-0670. II. Structure elucidation. J Antibiot (Tokyo) 52: 34-39]. Nevertheless, there is no additional similarity between lugdunin and the mentioned antibiotics, which makes the target prediction for lugdunin purely speculative. Since lugdunin exhibits bactericidal activity, its mode of action might differ from the other described peptides, whose activity is bacteriostatic.

Beside the use of purified peptide and derivatives thereof for eradication strategies also the preventive application of a lugdunin producer strain might be possible to e.g. clear *S. aureus* colonization in human noses.

---

Therefore, what is claimed, is:

1. Compound of the formula of:

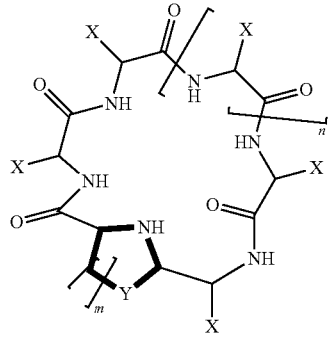
(I)

wherein

X is selected from the group consisting of: H, CH$_3$, CH$_2$CH$_3$,

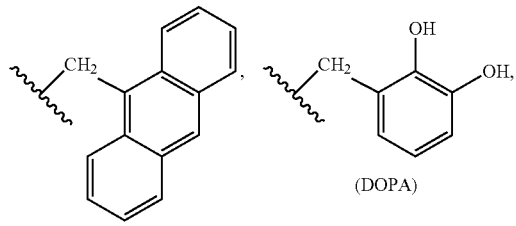

(anthranylalanine)    (DOPA)

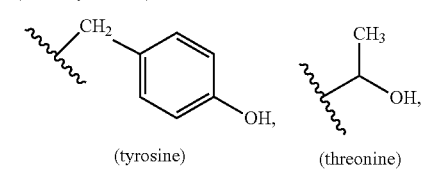

(tyrosine)    (threonine)

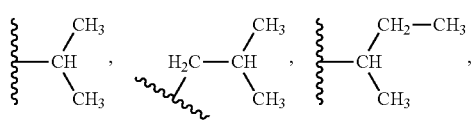

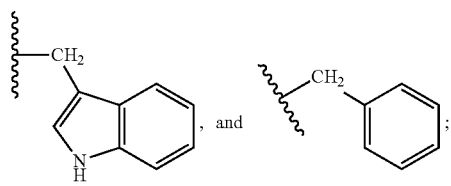

, and under the proviso that at least one X is:

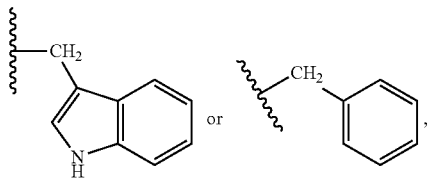 [SMILES: *Cc1c[nH]c2ccccc12 ; *Cc1ccccc1]
or and

Y is selected from the group consisting of O, S, and NH,
m is an integer from 1 to 3,
n is an integer from 0 to 4,
and the salts thereof, the solvates thereof and the solvates of the salts thereof,
further under the proviso that the compound is not a compound of formula (III)

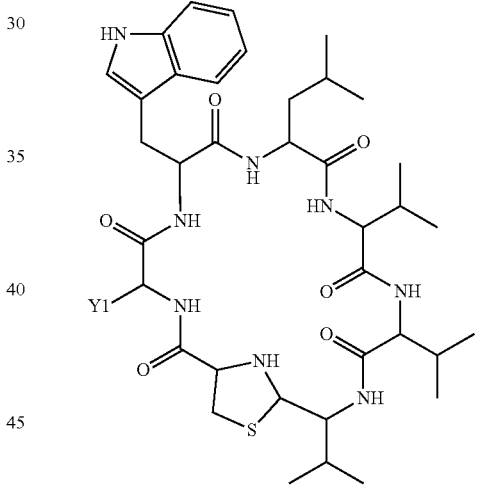

wherein Y1 is selected from the group consisting of

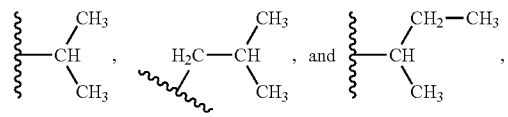

and further under the proviso that when m is 1, n is 2, and at least one X is

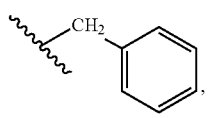 [SMILES: *Cc1ccccc1]

then at least two X are

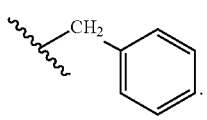

2. Compound of claim 1 comprising the following formula:

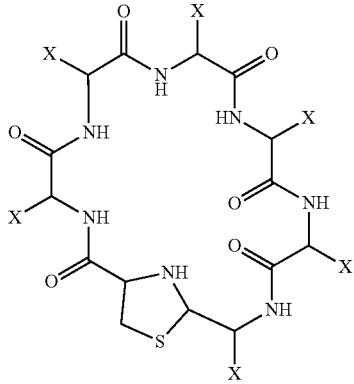
(II)

wherein

X is selected from the group consisting of: H, CH$_3$, CH$_2$CH$_3$, anthranylalanine, DOPA, tyrosine, threonine,

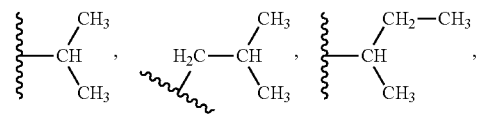

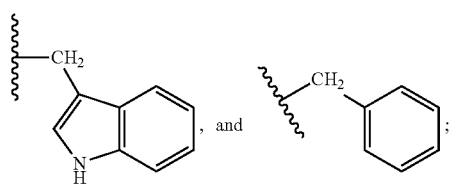

under the proviso that at least one X is:

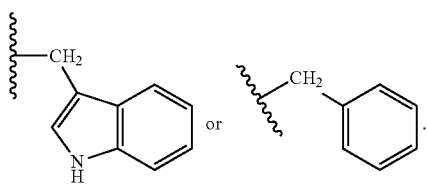 [SMILES: *Cc1c[nH]c2ccccc12 ; *Cc1ccccc1]

3. Pharmaceutical composition comprising the compound of claim 1 and a pharmaceutically acceptable carrier.

4. Method for the treatment or prophylaxis of a disease in a living being, comprising the administration to said living being of an antibacterially effective amount of the compound of formula (I),

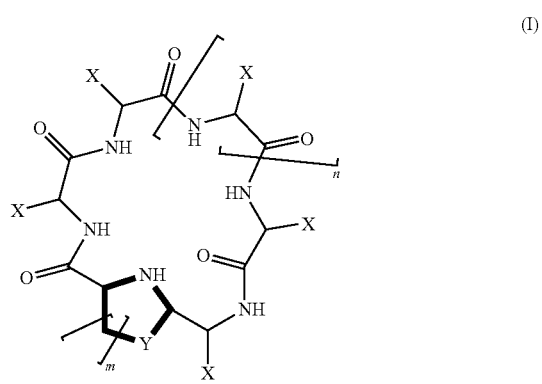
(I)

wherein

X is selected from the group consisting of: H, CH$_3$, CH$_2$CH$_3$,

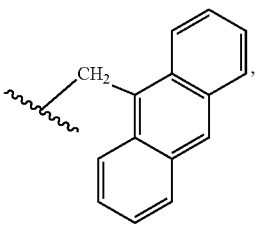

(anthranylalanine), (DOPA)

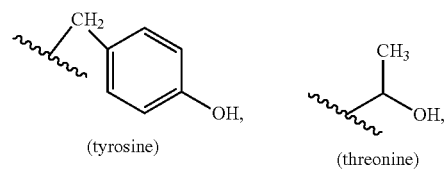

(tyrosine), (threonine)

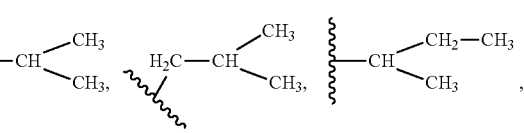

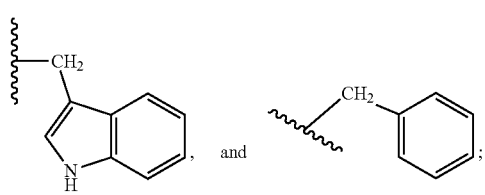
and under the proviso that at least one X is:

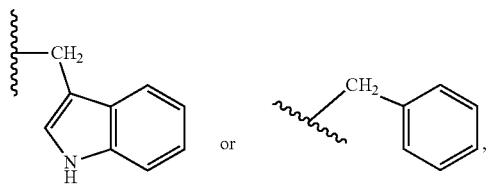 [SMILES: *Cc1c[nH]c2ccccc12 ; *Cc1ccccc1]

and
Y is selected from the group consisting of O, S, and NH,
m is an integer from 1 to 3,
n is an integer from 0 to 4,
and the salts thereof, the solvates thereof and the solvates of the salts thereof,
wherein the disease is selected from one or more members in the group of: infectious disease, bacterial disease, infection by a Gram-positive bacterium, infection by *Staphylococcus aureus*, infection by methicillin-resistant *Staphylococcus aureus* (MRSA), and infection by vancomycin-resistant *Staphylococcus aureus* (VRSA).

5. Method of producing the compound of formula (IV)

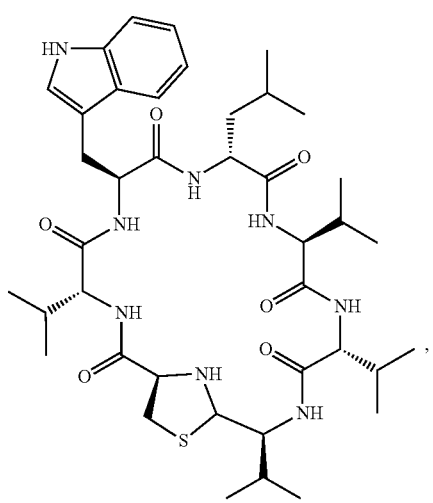

comprising the following steps:
(1) Providing bacteria of the species of *Staphylococcus lugdunensis*,
(2) Purifying the compound of formula (IV) from said bacteria.

6. The method of claim 5, wherein after step (1) and before step (2) the bacteria and a medium for the cultivation of the bacteria are extracted and the bacteria and medium extract are subjected to step (2) where the compound is purified from said bacteria and medium extract.

7. Method of claim 6, wherein in step (2) the purification involves the use of high performance liquid chromatography (HPLC) identifying a signal peak associated with said compound.

8. Method of claim 7, wherein said signal peak corresponds to a molecular mass which is selected from the group of ranges of molecular masses consisting of: approx. 650 Da-950 Da, approx. 700 Da-850 Da, approx. 750 Da-800 Da, approx. 770 Da-790 Da, and approx. 782.5 Da.

9. Method of producing the compound of formula (IV)

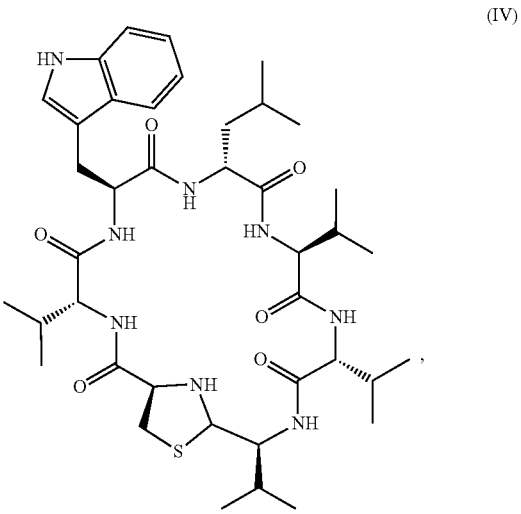 [SMILES: CC(C)C[C@H]1NC(=O)[C@H](Cc2c[nH]c3ccccc23)NC(=O)[C@@H](C(C)C)NC(=O)[C@@H]2CSC(N2)[C@H](C(C)C)NC(=O)[C@@H](C(C)C)NC(=O)[C@H](C(C)C)NC1=O ; ","]

comprising the following steps:
(1) Expressing the non-ribosomal peptide synthetase system II of the species of *Staphylococcus lugdunensis* (NRPS-II) in a biological system,
(2) Incubating the expressed NRPS-II under conditions allowing the synthesis of the compound of formula (IV),
(3) Purifying said compound.

10. Method of claim 9, wherein said NRPS-II is encoded by a nucleic acid molecule comprising any of the coding sequences of the genes lugA, lugB, lugC, and lugD.

11. Method of claim 10, wherein said nucleic acid molecule further comprises at least one element selected from the group consisting of: transcriptional regulator of GntR family, ABC transporter, ABC-2 type transport system permease protein, hyp. membrane protein, TetR/AcrR family regulator, Thioesterase family protein, 4'-phosphopantetheinyltransferase, and put. negative regulator of sigY.

12. Method of claim 10, wherein the conditions comprise amino acids, thioesterase, and buffer.

13. A pharmaceutically acceptable composition comprising a compound of the formula (I):

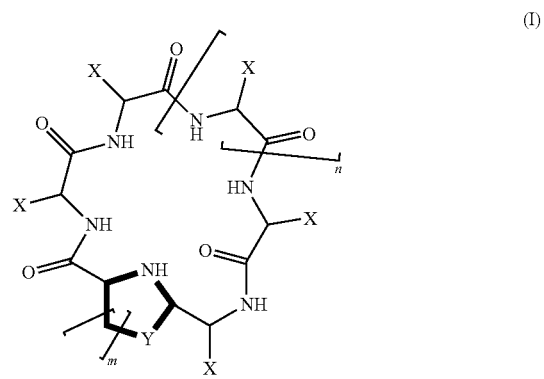

wherein
X is selected from the group consisting of: H, CH$_3$, CH$_2$CH$_3$,

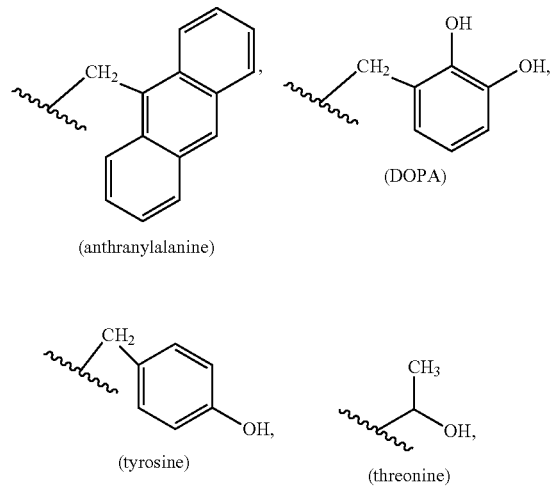

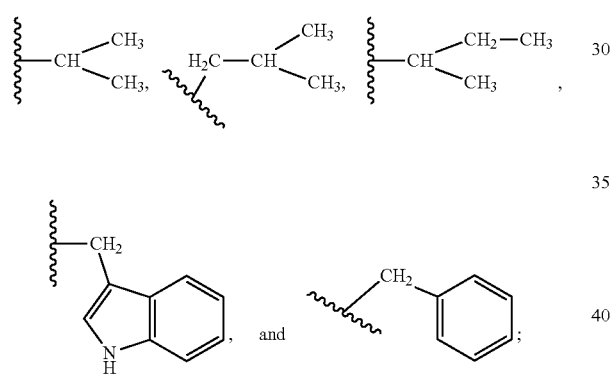

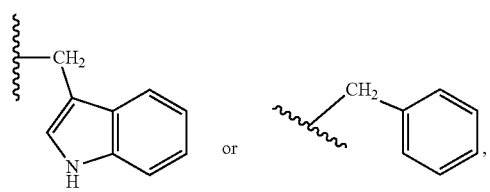 [SMILES: *Cc1c[nH]c2ccccc12 ; *Cc1ccccc1]

under the proviso that at least one X is:

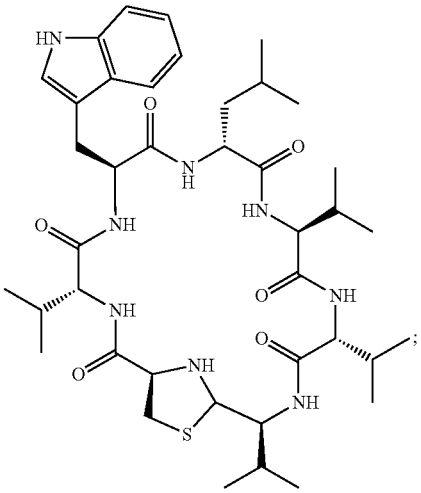

and the salts thereof, the solvates thereof and the solvates of the salts thereof, and a pharmaceutically acceptable carrier.

14. The composition of claim 13, wherein the compound is according to formula (II):

(II)

wherein
X is selected from the group consisting of: H, CH3, CH2CH3, anthranylalanine, DOPA, tyrosine, threonine,

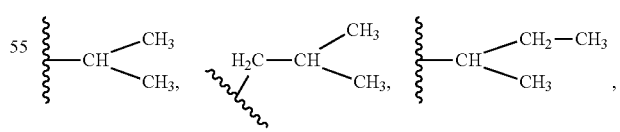

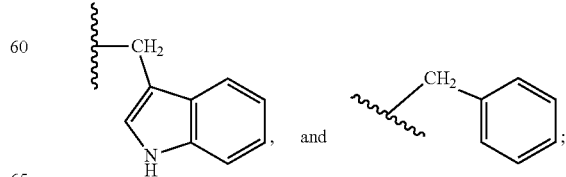

and
Y is selected from the group consisting of O, S, and NH,
m is an integer from 1 to 3,
n is an integer from 0 to 4,
and further under the proviso that the compound is not the compound of formula (IV)

under the proviso that at least one X is:

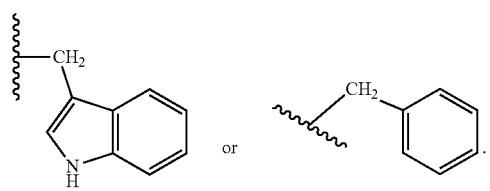 [SMILES: *Cc1c[nH]c2ccccc12 ; *Cc1ccccc1]

or

15. The composition of claim 13, wherein the compound is according to formula (III):

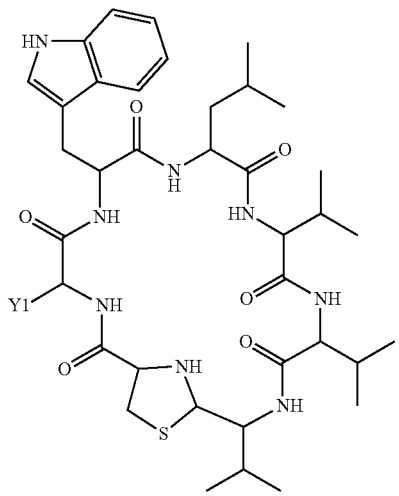

(III)

wherein
Y1 is selected from the group consisting of:

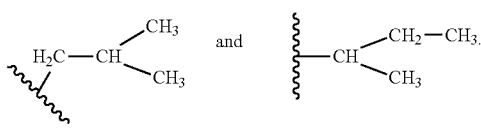

and

16. The method of claim 4, wherein the compound is according to formula (III):

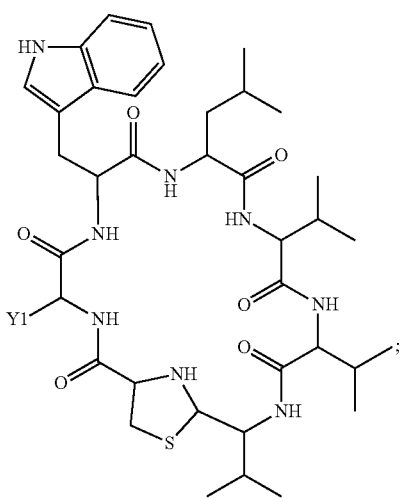

(III)

wherein
Y1 is selected from the group consisting of:

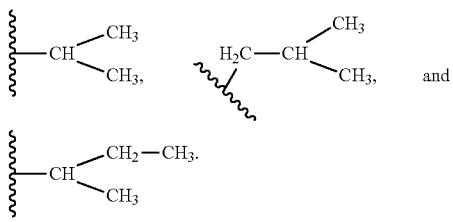

and

17. The method of claim 4, wherein the compound is the compound of formula (IV):

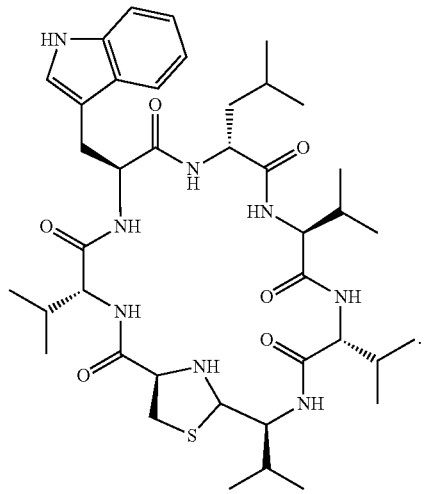

(IV)

18. The method of claim 4, wherein the disease is infection by a Gram-positive bacterium.

19. The method of claim 4, wherein the disease is infection by *Staphylococcus aureus*.

20. The method of claim 4, wherein the disease is infection by methicillin-resistant *Staphylococcus aureus* (MRSA).

21. The method of claim 4, wherein the disease is infection by vancomycin-resistant *Staphylococcus aureus* (VRSA).

22. The method of claim 17, wherein the disease is infection by a Gram-positive bacterium.

23. The method of claim 17, wherein the disease is infection by *Staphylococcus aureus*.

24. The method of claim 17, wherein the disease is infection by methicillin-resistant *Staphylococcus aureus* (MRSA).

25. The method of claim 17, wherein the disease is infection by vancomycin-resistant *Staphylococcus aureus* (VRSA).

26. A compound of the formula of:

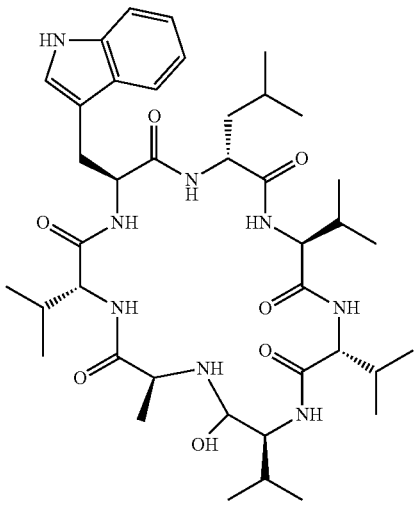

(V)

and the salts thereof, the solvates thereof and the solvates of the salts thereof.

27. Pharmaceutical composition comprising the compound of claim 26 and a pharmaceutically acceptable carrier 28. A compound of the formula of

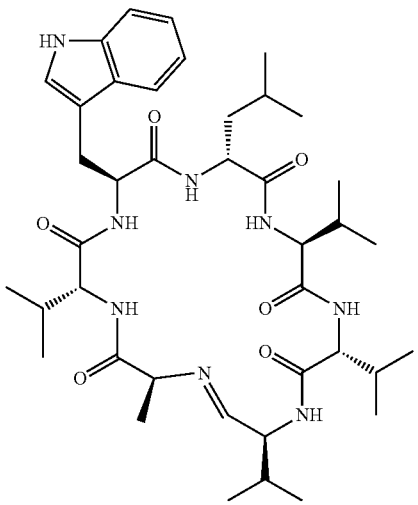

(VI)

and the salts thereof, the solvates thereof and the solvates of the salts thereof.

29. Pharmaceutical composition comprising the compound of claim 27 and a pharmaceutically acceptable carrier.

30. Method for the treatment or prophylaxis of a disease in a living being, comprising the administration to said living being of an antibacterially effective amount of the compound of formula (V),

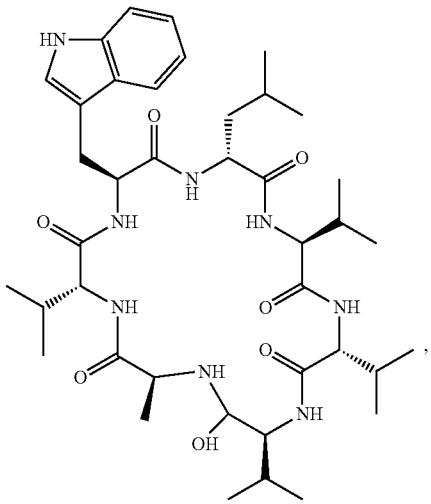

(V)

wherein the disease is selected from one or more members in the group of: infectious disease, bacterial disease, infection by a Gram-positive bacterium, infection by Staphylococcus aureus, infection by methicillin-resistant Staphylococcus aureus (MRSA), and infection by vancomycin-resistant Staphylococcus aureus (VRSA).

31. Method for the treatment or prophylaxis of a disease in a living being, comprising the administration to said living being of an antibacterially effective amount of the compound of formula (VI),

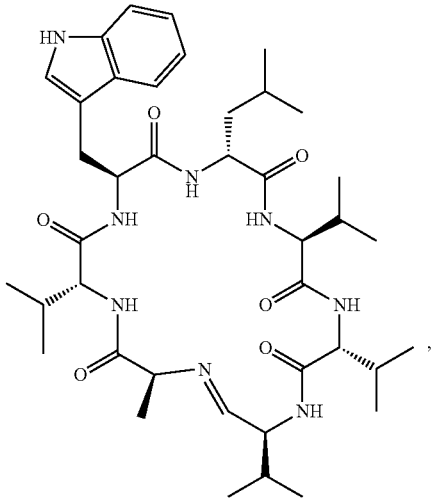

(VI)

wherein the disease is selected from one or more members in the group of: infectious disease, bacterial disease, infection by a Gram-positive bacterium, infection by Staphylococcus aureus, infection by methicillin-resistant Staphylococcus aureus (MRSA), and infection by vancomycin-resistant Staphylococcus aureus (VRSA).

* * * * *